United States Patent
Miyake et al.

(10) Patent No.: US 11,819,354 B2
(45) Date of Patent: Nov. 21, 2023

(54) TRANSMISSION APPARATUS, RADIATION IMAGING SYSTEM, AND TRANSMISSION CONTROL APPARATUS

(71) Applicant: Konica Minolta, Inc., Tokyo (JP)

(72) Inventors: Nobuyuki Miyake, Kanagawa (JP); Kentaro Hara, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 98 days.

(21) Appl. No.: 17/178,788

(22) Filed: Feb. 18, 2021

(65) Prior Publication Data

US 2021/0251596 A1    Aug. 19, 2021

(30) Foreign Application Priority Data

Feb. 19, 2020  (JP) ................................ 2020-025992
Feb. 21, 2020  (JP) ................................ 2020-028039

(51) Int. Cl.
*A61B 6/00* (2006.01)

(52) U.S. Cl.
CPC .............. *A61B 6/542* (2013.01); *A61B 6/545* (2013.01); *A61B 6/548* (2013.01)

(58) Field of Classification Search
CPC ........... A61B 6/542; A61B 6/54; A61B 6/548; A61B 6/46; A61B 6/545; A61B 6/582; A61B 6/4233; A61B 6/56; A61B 6/5258; A61B 6/463; A61B 6/482; A61B 6/547; A61B 6/5205; A61B 6/488; A61B 6/4405; A61B 6/4452; A61B 6/467; A61B 6/563; A61B 6/08; A61B 6/40; A61B 6/5294; A61B 6/5241; A61B 6/468; A61B 6/588; A61B 6/587; A61B 6/544; A61B 6/589; A61B 6/469; A61B 2560/0271; A61B 6/585; A61B 6/032; A61B 6/5235;

(Continued)

(56) References Cited

U.S. PATENT DOCUMENTS 7,082,339 B2 * 7/2006 Murray ................. H04L 12/282
                                                    700/282
2011/0291800 A1 * 12/2011 Butzine ................. A61B 6/468
                                                    340/8.1

(Continued)

FOREIGN PATENT DOCUMENTS

JP   H07275234 A   10/1995
JP   2007229346 A   9/2007
(Continued)

OTHER PUBLICATIONS

JPO Notice of Reasons for Refusal for corresponding JP Application No. 2020-025992; dated Sep. 5, 2023.

*Primary Examiner* — Irakli Kiknadze
(74) *Attorney, Agent, or Firm* — CANTOR COLBURN LLP

(57) ABSTRACT

A transmission apparatus includes a transmission unit that transmits an operation state of a radiation imaging system to a user and a hardware processor that controls a state of the transmission unit, and the hardware processor controls the state of the transmission unit such that the state of the transmission unit is a state based on that at a time of the imaging of the exposure image between the first exposure and the second exposure when imaging the exposure image in the radiation imaging system.

17 Claims, 12 Drawing Sheets

(58) Field of Classification Search
CPC ....... A61B 6/4028; A61B 6/42; A61B 6/4035; A61B 6/5217; A61B 6/484; A61B 6/4291; A61B 6/483; A61B 6/06; A61B 6/4283; A61B 6/145; A61B 6/508; A61B 6/4488; A61B 6/14; A61B 6/4225; A61B 6/566; A61B 6/4266; A61B 6/4411; A61B 6/4441; A61B 6/465; G01N 23/04; G01N 2223/303; G01N 2223/306; G01N 2223/304; H04N 5/32; H04N 7/18; H04N 9/8205; H04N 5/77; H04N 25/713; H04N 23/81; H04N 25/76; H04N 25/75; G06T 11/006; G06T 11/005; G06T 11/00; G06T 7/0012; G16H 50/30; G01T 1/02; G01T 1/17; G01T 1/161; G01T 1/247; H05G 1/10; H05G 1/08; H05G 1/06; H05G 1/42; H05G 1/26; H05G 1/12; H05G 1/52; H05G 1/44; H05G 1/46; H05G 1/40; H05G 1/34; Y10T 403/32262; H01L 27/14663; H01L 27/14676
USPC .......................................................... 378/62
See application file for complete search history.

(56) References Cited

U.S. PATENT DOCUMENTS

| 2014/0064448 | A1* | 3/2014 | Ito | A61B 6/542 |
| | | | | 378/97 |
| 2015/0164460 | A1* | 6/2015 | Liu | A61B 6/032 |
| | | | | 378/20 |
| 2016/0262716 | A1* | 9/2016 | Kravis | A61B 6/547 |
| 2018/0000442 | A1* | 1/2018 | Hiroike | A61B 6/54 |
| 2020/0155108 | A1* | 5/2020 | Saigusa | A61B 6/4283 |

FOREIGN PATENT DOCUMENTS

| JP | 2019013672 A | 1/2019 |
| JP | 2019126709 A | 8/2019 |

* cited by examiner

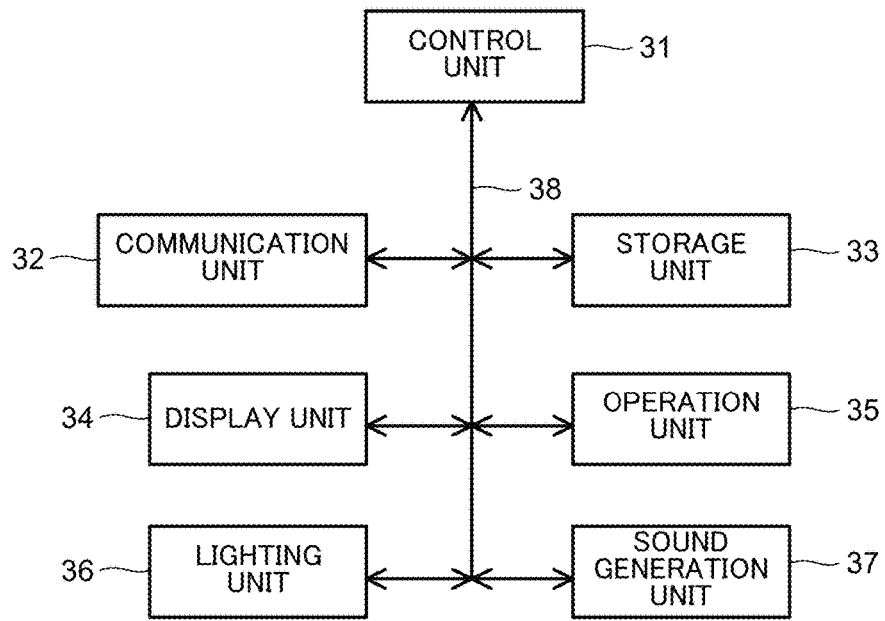

FIG. 3

| OPERATION STATE | BEFORE IMAGING START OF PRELIMINARY EXPOSURE IMAGE | DURING IMAGING OF PRELIMINARY EXPOSURE IMAGE | BETWEEN PRELIMINARY EXPOSURE AND MAIN EXPOSURE | DURING IMAGING OF MAIN EXPOSURE IMAGE | AFTER IMAGING END OF MAIN EXPOSURE IMAGE |
|---|---|---|---|---|---|
| LIGHTING UNIT | TURN OFF | TURN ON | TURN ON | TURN ON | TURN OFF |
| SOUND GENERATION UNIT | NO SOUND | OUTPUT SOUND | OUTPUT SOUND | OUTPUT SOUND | NO SOUND |

FIG. 4

| OPERATION STATE | BEFORE IMAGING START OF PRELIMINARY EXPOSURE IMAGE | DURING IMAGING OF PRELIMINARY EXPOSURE IMAGE | BETWEEN PRELIMINARY EXPOSURE AND MAIN EXPOSURE | DURING IMAGING OF MAIN EXPOSURE IMAGE | AFTER IMAGING END OF MAIN EXPOSURE IMAGE |
|---|---|---|---|---|---|
| LIGHTING UNIT | TURN OFF | TURN ON | TURN OFF | TURN ON | TURN OFF |
| SOUND GENERATION UNIT | NO SOUND | OUTPUT SOUND | NO SOUND | OUTPUT SOUND | NO SOUND |

FIG. 5

| OPERATION STATE | BEFORE IMAGING START OF PRELIMINARY EXPOSURE IMAGE | DURING IMAGING OF PRELIMINARY EXPOSURE IMAGE | BETWEEN PRELIMINARY EXPOSURE AND MAIN EXPOSURE | DURING IMAGING OF MAIN EXPOSURE IMAGE | AFTER IMAGING END OF MAIN EXPOSURE IMAGE |
|---|---|---|---|---|---|
| LIGHTING UNIT | TURN OFF | TURN ON | TURN OFF | TURN ON | TURN OFF |
| SOUND GENERATION UNIT | NO SOUND | OUTPUT SOUND | OUTPUT SOUND | OUTPUT SOUND | NO SOUND |

FIG. 6

| OPERATION STATE | BEFORE IMAGING START OF PRELIMINARY EXPOSURE IMAGE | DURING IMAGING OF PRELIMINARY EXPOSURE IMAGE | BETWEEN PRELIMINARY EXPOSURE AND MAIN EXPOSURE | DURING IMAGING OF MAIN EXPOSURE IMAGE | AFTER IMAGING END OF MAIN EXPOSURE IMAGE |
|---|---|---|---|---|---|
| LIGHTING UNIT | TURN OFF | TURN ON | TURN ON | TURN ON | TURN OFF |
| SOUND GENERATION UNIT | NO SOUND | OUTPUT SOUND | NO SOUND | OUTPUT SOUND | NO SOUND |

FIG. 7

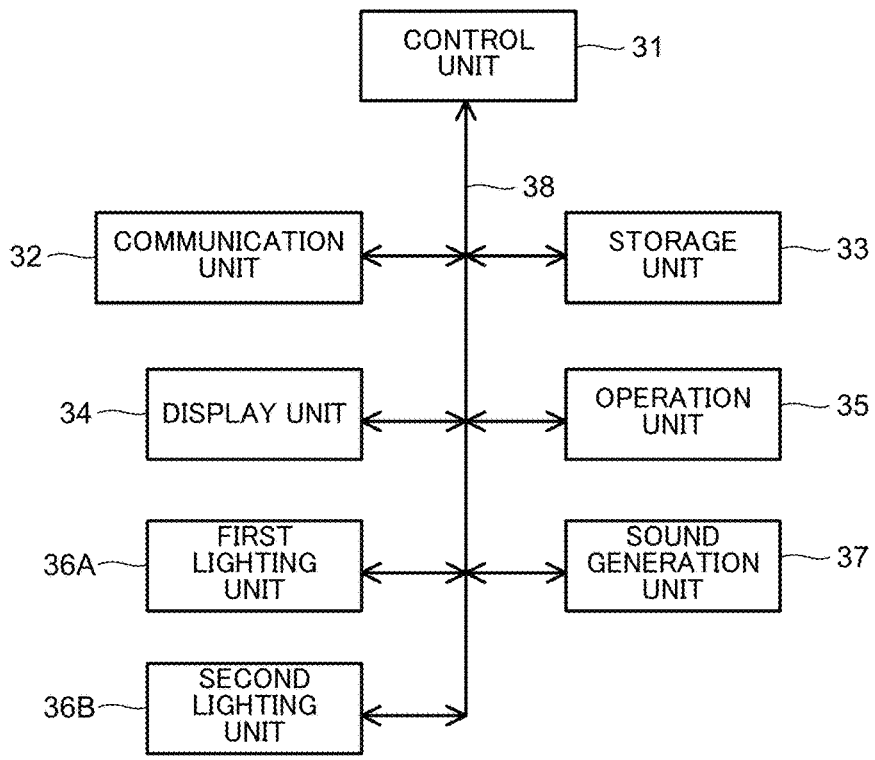

FIG. 8

| OPERATION STATE | BEFORE IMAGING START OF PRELIMINARY EXPOSURE IMAGE | DURING IMAGING OF PRELIMINARY EXPOSURE IMAGE | BETWEEN PRELIMINARY EXPOSURE AND MAIN EXPOSURE | DURING IMAGING OF MAIN EXPOSURE IMAGE | AFTER IMAGING END OF MAIN EXPOSURE IMAGE |
|---|---|---|---|---|---|
| FIRST LIGHTING UNIT | TURN OFF | TURN ON | TURN ON | TURN ON | TURN OFF |
| SECOND LIGHTING UNIT | TURN OFF | TURN ON | TURN OFF | TURN ON | TURN OFF |
| SOUND GENERATION UNIT | NO SOUND | OUTPUT SOUND | OUTPUT SOUND | OUTPUT SOUND | NO SOUND |

FIG. 9

| | START PREPARATION OF IMAGING | START IMAGING OF PRELIMINARY EXPOSURE IMAGE | | END IMAGING OF MAIN EXPOSURE IMAGE | |
|---|---|---|---|---|---|
| OPERATION STATE | BEFORE IMAGING START OF PRELIMINARY EXPOSURE IMAGE | DURING IMAGING OF PRELIMINARY EXPOSURE IMAGE | BETWEEN PRELIMINARY EXPOSURE AND MAIN EXPOSURE | DURING IMAGING OF MAIN EXPOSURE IMAGE | AFTER IMAGING END OF MAIN EXPOSURE IMAGE |
| LIGHTING UNIT | TURN OFF | TURN ON | TURN ON | TURN ON | TURN OFF |
| SOUND GENERATION UNIT | NO SOUND | OUTPUT SOUND | OUTPUT SOUND | OUTPUT SOUND | NO SOUND |

FIG. 11

| | UNDER PREPARATION OF IMAGING (DURING NON-EXPOSURE) | DURING IMAGING (DURING EXPOSURE) | UNDER PREPARATION OF IMAGING (DURING NON-EXPOSURE) | | DURING IMAGING (DURING EXPOSURE) | | DURING IMAGING (DURING EXPOSURE) |
|---|---|---|---|---|---|---|---|
| OPERATION STATE | BEFORE IMAGING START OF PRELIMINARY EXPOSURE IMAGE | DURING IMAGING OF PRELIMINARY EXPOSURE IMAGE | | BETWEEN PRELIMINARY EXPOSURE AND MAIN EXPOSURE | DURING IMAGING OF MAIN EXPOSURE IMAGE | | AFTER IMAGING END OF MAIN EXPOSURE IMAGE |
| FIRST LIGHTING UNIT | TURN OFF | TURN ON | | TURN ON | TURN ON | | TURN OFF |
| SECOND LIGHTING UNIT | TURN OFF | TURN OFF | TURN ON | TURN OFF | TURN OFF | TURN ON | TURN OFF |
| SOUND GENERATION UNIT | NO SOUND | NO SOUND | OUTPUT SOUND | NO SOUND | NO SOUND | OUTPUT SOUND | NO SOUND |

FIG. 12

| No | IMAGING AREA | IMAGING DIRECTION | PREDETERMINED TIME |
|---|---|---|---|
| 1 | CHEST | FRONT | 5 SECONDS |
| 2 | CHEST | SIDE | 5 SECONDS |
| 3 | HAND | FRONT | 10 SECONDS |
| . | . | . | . |
| . | . | . | . |
| . | . | . | . |

| No | IMAGING AREA | IMAGING DIRECTION | PREDETERMINED TIME | DISEASE CORRECTION | AGE CORRECTION |
|---|---|---|---|---|---|
| 1 | CHEST | FRONT | 5 SECONDS | RESPIRATORY DISEASE −2 SECONDS | 75 YEARS OLD OR OLDER −1 SECOND 3 YEARS OLD OR YOUNGER −1 SECOND |
| 2 | CHEST | SIDE | 5 SECONDS | RESPIRATORY DISEASE −2 SECONDS | 75 YEARS OLD OR OLDER −1 SECOND 3 YEARS OLD OR YOUNGER −1 SECOND |
| 3 | HAND | FRONT | 8 SECONDS | TREMOR −7 SECONDS | NONE |
| ⋮ | ⋮ | ⋮ | ⋮ | ⋮ | ⋮ |

FIG. 21

| KIND OF APPARATUS | COMMUNICATION METHOD | TRANSFER TIME OF PRELIMINARY EXPOSURE IMAGE | STANDARD DEVIATION $1\sigma$ | MAXIMUM TIME FOR PREPARATION OF MAIN EXPOSURE CONDITION |
|---|---|---|---|---|
| A | WIRELESS LAN | 1 SECOND | 0.2 SECONDS | 0.5 SECONDS |
| A | WIRED LAN | 0.3 SECONDS | 0.1 SECONDS | 0.5 SECONDS |
| B | WIRELESS LAN | 2 SECONDS | 0.4 SECONDS | 0.5 SECONDS |
| B | WIRED LAN | 0.5 SECONDS | 0.2 SECONDS | 0.5 SECONDS |

FIG. 22

| KIND OF APPARATUS | COMMUNICATION METHOD | PREDETERMINED TIME | CALCULATION OF PREDETERMINED TIME |
|---|---|---|---|
| A | WIRELESS LAN | 2.5 SECONDS | 1+0.2×5+0.5=2.5 SECONDS |
| A | WIRED LAN | 1.3 SECONDS | 0.3+0.1×5+0.5=1.3 SECONDS |
| B | WIRELESS LAN | 4.5 SECONDS | 2+0.4×5+0.5=4.5 SECONDS |
| B | WIRED LAN | 2.0 SECONDS | 0.5+0.2×5+0.5=2.0 SECONDS |

FIG. 23

TRANSMISSION APPARATUS, RADIATION IMAGING SYSTEM, AND TRANSMISSION CONTROL APPARATUS

CROSS REFERENCE TO RELATED APPLICATIONS

The present invention claims priority under 35 U.S.C. § 119 to Japanese Patent Application No. 2020-025992, filed on Feb. 19, 2020, and the Japanese Patent Application No. 2020-028039, filed on Feb. 21, 2020, the entire content of which is incorporated herein by reference.

BACKGROUND

Technological Field

The present invention relates to a transmission apparatus, a radiation imaging system, and a transmission control apparatus.

Description of Related Art

Commonly known radiation imaging systems include one that performs a plurality of exposures including a first exposure and a second exposure, such as, one that includes an automatic exposure control function that performs a main exposure and a preliminary exposure prior to the main exposure when taking radiation images. In the automatic exposure control function, the preliminary exposure is performed at a dose lower than that of the main exposure, and the imaging conditions such as the dose for the main exposure are determined based on the obtained image in the preliminary exposure (hereinafter also referred to as "preliminary exposure image") and the incidental information associated with the preliminary exposure image (for example, the irradiation time in the preliminary exposure).

In such a radiation imaging system, a configuration, in which an imaging status is transmitted to a user so that the user (e.g., a radiographer or a patient) can recognize whether an exposure image is in the state during or after imaging has been known. Generally known configurations include one in which a light indicating that imaging in progress is turned on during imaging and the light is turned off after end of imaging, and one in which a buzzer is sounded during imaging and the buzzer is turned off after end of imaging.

In one example, a configuration that displays a guidance to a patient upon pressing of a first-stage switch and displays a completion guidance when irradiation is ended is disclosed in Japanese Patent Application Laid-Open No. 2007-229346.

SUMMARY

Incidentally, in the configuration having, for example, an automatic exposure control function that performs a preliminary exposure and a main exposure, when a transfer time of an exposure image obtained by the first exposure (the preliminary exposure) or an image analyzing time extend, deriving of an imaging condition of the second exposure (the main exposure) is delayed accordingly, and thereby, an imaging time extends as a whole. For this reason, the user recognizes transmission or non-transmission of the imaging state between the first exposure and the second exposure.

Thus, a patient may mistake the end of the first exposure for the end of the second exposure and may move his or her body before the second exposure, which may lead to imaging failures due to body movement of the patient. A radiographer may mistake the end of the first exposure for the end of the second exposure and may stop imaging, which may lead to imaging failures.

In the configuration disclosed in Japanese Patent Application Laid-Open No. 2007-229346, a guidance of end is displayed between the first exposure and the second exposure, and thus, the problem cannot be solved.

Objects of the present invention are to provide a transmission apparatus, a radiation imaging system, and a transmission control apparatus capable of suppressing a user from mistaking the end of the first exposure for that of the second exposure.

To achieve at least one of the above objects, a transmission apparatus reflecting one aspect of the present invention includes: a transmission unit that transmits an operation state of a radiation imaging system to a user; and a hardware processor that controls a state of the transmission unit, in which when imaging an exposure image by an exposure including a first exposure and a second exposure in the radiation imaging system, the hardware processor controls the state of the transmission unit such that the state of the transmission unit is a state based on that at a time of the imaging of the exposure image between the first exposure and the second exposure.

To achieve at least one of the above objects, a radiation imaging system reflecting one aspect of the present invention includes: a radiation irradiation apparatus that emits radiation for exposure; a radiation imaging apparatus that generates image data of an exposure image by receiving an exposure of the radiation; and the transmission apparatus.

To achieve at least one of the above objects, a transmission control apparatus reflecting one aspect of the present invention that controls a transmission unit, which transmits an operation state of a radiation imaging system to a user includes; a hardware processor that decides a state of the transmission unit and controls the transmission unit such that the transmission unit is in the decided state of the transmission unit, in which when imaging an exposure image by an exposure including a first exposure and a second exposure in the radiation imaging system, the hardware processor sets a state based on that at a time of imaging of the exposure image to be a state of the transmission unit between the first exposure and the second exposure.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 3 is a block diagram of a specific configuration of a console;

FIG. 4 illustrates an exemplary state of transmission unit for each operation state of the radiation imaging system;

FIG. 5 illustrates a state of transmission unit for each operation state of a conventional radiation imaging system;

FIG. 6 illustrates another exemplary state of transmission unit for each operation state of the radiation imaging system;

FIG. 7 illustrates still another exemplary state of transmission unit for each operation state of the radiation imaging system;

FIG. 8 is a block diagram of a specific configuration of a console according to a variation;

FIG. 9 illustrates still another exemplary state of transmission unit for each operation state of the radiation imaging system;

FIG. 11 illustrates another exemplary state of transmission unit related to the radiation irradiation apparatus for each operation state of the radiation imaging system;

FIG. 12 illustrates another exemplary state of transmission unit related to the console for each operation state of the radiation imaging system;

FIG. 21 illustrates an exemplary table that contains a measurement time associated with an imaging region and an imaging direction;

FIG. 22 illustrates an exemplary table that contains a calculation parameter of a measurement time associated with a kind of apparatus and a communication method, and FIG. 23 illustrates an exemplary table that contains a calculation result of the table illustrated in FIG. 22.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
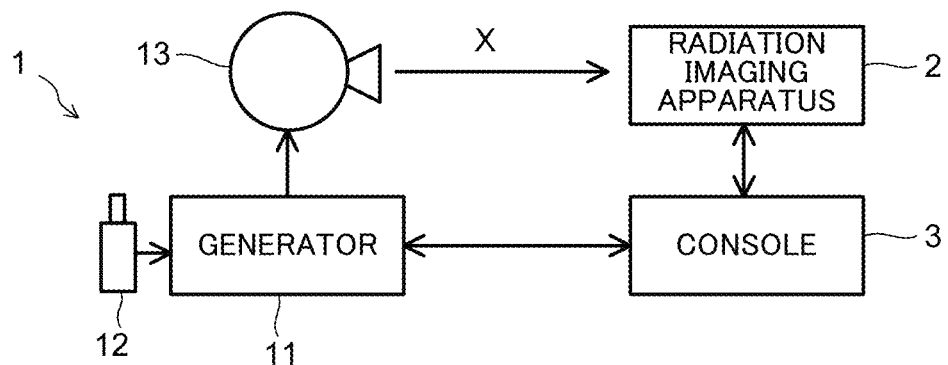
FIG. 1 is a block diagram of a configuration of a radiation imaging system according to a first embodiment of the present invention.

Hereinafter, a first embodiment of the present invention will be described with reference to the drawings. FIG. 1 is a block diagram of a configuration of radiation imaging system 100 according to the first embodiment of the present invention.

As illustrated in FIG. 1, radiation imaging system 100 according to the present embodiment is configured to include radiation irradiation apparatus 1, radiation imaging apparatus 2, and console 3. Further, radiation imaging system 100 is connectable to, for example, Radiology Information System (RIS) and Picture Archiving and Communication System (PACS) and/or the like (not illustrated).

Radiation irradiation apparatus 1 is connected to console 3 so as to be able to communicate thereto by wire or wirelessly. Further, radiation irradiation apparatus 1 is configured to include generator 11, exposure switch 12 and radiation source 13.

Generator 11 is capable of applying a voltage in accordance with preset radiation exposure conditions (for example, tube voltage, tube current, irradiation time, product of tube current and time (mAs-value)—hereinafter also referred to as "tube current time product")—to radiation source 13, based on the operation of exposure switch 12.

Radiation source 13 (tube bulb) includes a rotating anode and a filament and the like (not illustrated). When generator 11 applies a voltage, the filament irradiates the rotating anode with an electron beam corresponding to the applied voltage, and the rotating anode then generates radiation X (for example, X-ray) with a dose corresponding to the intensity of the electron beam.

FIG. 1 illustrates an example including separated generator 11, exposure switch 12 and radiation source 13, but the components may be integrally configured. FIG. 1 illustrates an example including exposure switch 12 connected to generator 11, but exposure switch 12 may be provided in another apparatus. Radiation irradiation apparatus 1 may be installed in an imaging room, or may be configured to be movable by being incorporated in a nursing cart for examination or the like.

Radiation imaging apparatus 2 is connected to console 3 so as to be able to communicate thereto by wire or wirelessly. Radiation imaging apparatus 2 is configured such that it can generate image data of an exposure image of a subject by receiving radiation X exposure through the subject from radiation irradiation apparatus 1.

Figure 2:
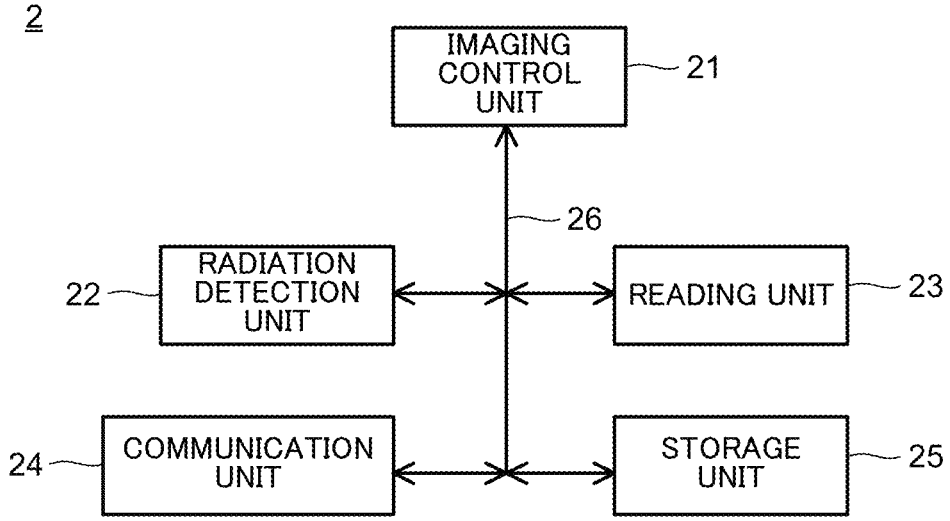
FIG. 2 is a block diagram of a specific configuration of a radiation imaging apparatus.

As illustrated in FIG. 2, radiation imaging apparatus 2 includes imaging control unit 21, radiation detection unit 22, reading unit 23, communication unit 24, storage unit 25, and bus 26 connecting each unit.

Imaging control unit 21 includes a central processing unit (CPU), a random access memory (RAM), and the like. The CPU of imaging control unit 21 reads various programs stored in storage unit 25, loads the programs in the RAM, executes various kinds of processing according to the loaded programs, and centrally controls the behavior of each unit in the radiation imaging apparatus 2 based on a control signal or the like received from an external apparatus such as console 3.

Radiation detection unit 22 includes a substrate in which pixels equipped with a switch element and a radiation detection element generating electric charge according to a dose by receiving radiation X are arranged in a two-dimensional shape (matrix shape).

Reading unit 23 is capable of reading the amount of the electric charge discharged from each pixel as a signal value, and generating image data from a plurality of signal values.

Communication unit 24 is capable of receiving various control signals, various kinds of data and the like from an external apparatus, and transmitting various control signals, generated image data and the like to the external apparatus.

Storage unit 25 includes a nonvolatile semiconductor memory, a hard disk and the like, and stores various programs to be executed by imaging control unit 21, parameters necessary for the execution of the programs, and the like. Storage unit 25 is also capable of storing image data generated by reading unit 23 and various kinds of data processed by imaging control unit 21.

With imaging control unit 21 turning off the switch elements of radiation detection unit 22, radiation imaging apparatus 2 having the above described configuration accumulates electric charge in each pixel according to the radiation dose upon receiving radiation exposure. When imaging control unit 21 turns on each switch element and the electric charge is discharged from each pixel, reading unit 23 converts each electric charge amount into a signal value and reads it out as image data.

Radiation imaging apparatus 2 may have a configuration such that a scintillator or the like is incorporated, the scintillator converts emitted radiation X into light with another wavelength such as visible light, and electric charge according to the converted light is generated, or a configuration such that the electric charge is directly generated from radiation X without passing through the scintillator or the like. Radiation imaging apparatus 2 may be a dedicated machine type integrated with an imaging table, or a portable type.

As illustrated in FIG. 1, console 3 includes a Personal Computer (PC), a portable terminal or a dedicated apparatus, and is connected to, for example, radiation irradiation apparatus 1 and radiation imaging apparatus 2 so as to be able to communicate thereto by wire or wirelessly. Console 3 can set, for example, the imaging conditions of radiation irradiation apparatus 1 and radiation imaging apparatus 2, the imaging target area, and the like based on the imaging order from an external apparatus (RIS or the like) or the operation from a user. Console 3 corresponds to "transmission apparatus" of the present invention.

As illustrated in FIG. 3, console 3 includes control unit 31, communication unit 32, storage unit 33, display unit 34, operation unit 35, lighting unit 36, sound generation unit 37, and bus 38 connecting each unit.

Control unit 31 includes a CPU, a RAM and the like. The CPU of control unit 31 reads various programs stored in storage unit 33 according to the operation from operation unit 35, loads the programs in the RAM, executes various kinds of processing according to the loaded programs, and centrally controls the behavior of respective units of console 3.

Communication unit 32 includes a LAN adapter, a modem, a terminal adapter (TA) and the like, and controls data transmission and reception with each apparatus connected to a communication network.

Storage unit 33 includes a nonvolatile semiconductor memory, a hard disk and the like, and stores various programs to be executed by control unit 31, parameters necessary for the execution of the programs, and the like. Further, storage unit 33 can store the image data received from radiation imaging apparatus 2 and the image data processed by control unit 31 so that the image date associates with the incidental information.

Display unit 34 includes a monitor such as Liquid Crystal Display (LCD) or Cathode Ray Tube (CRT) and displays input instruction, data and the like from operation unit 35 according to the instruction of a display signal input from control unit 31.

Operation unit 35 is configured to include a keyboard provided with cursor keys, numeric input keys, various function keys and the like, and a pointing device such as a mouse. Operation unit 35 outputs an instruction signal input by a key operation via the keyboard or a mouse operation to control unit 31. Operation unit 35 may be provided with a touch panel on the display screen of display unit 34, and, in this case, operation unit 35 outputs an instruction signal input through the touch panel to control unit 31.

Lighting unit 36 is a lighting device (e.g., a lamp) to transmit an operation state of radiation imaging system 100 to the user. More specifically, lighting unit 36 turns on during imaging by radiation imaging system 100 and turns off during non-imaging by radiation imaging system 100 under the control of control unit 31. In other words, lighting unit 36 transmits the operation state of radiation imaging system 100 to the user by using a method acting on a visual sense of the user. Lighting unit 36 corresponds to "transmitter" of the present invention.

Sound generation unit 37 is a sound generation device (e.g., a device to generate an alarm such as a buzzer) to transmit an operation state of radiation imaging system 100 to the user. More specifically, sound generation unit 37 outputs the sound during imaging by radiation imaging system 100 and does not output the sound during non-imaging by radiation imaging system 100 under the control of control unit 31. In other words, sound generation unit 37 transmits the operation state of radiation imaging system 100 to the user by using a method acting on an auditory sense of the user. Sound generation unit 37 corresponds to "transmitter" of the present invention.

Next, a control by control unit 31 in radiation imaging system 100 will be described. Control unit 31 performs automatic exposure control to determine an imaging condition for performing the main exposure (the second exposure) based on the preliminary exposure image obtained by the preliminary exposure (the first exposure) and the incidental information related to the preliminary exposure image. The preliminary exposure is performed prior to the main exposure at a dose lower than that of the main exposure.

Control unit 31 determines states of lighting unit 36 and sound generation unit 37 between the periods during the imaging and the non-imaging of the exposure image to control lighting unit 36 and sound generation unit 37 so that the units are to be in a determined state. Control unit 31 corresponds to "transmission control apparatus" and "decision unit". FIG. 4 illustrates a state of transmission unit for each operation state of the radiation imaging system.

As illustrated in FIG. 4, control unit 31 varies the states of lighting unit 36 and sound generation unit 37 between the periods during exposure and non-exposure. More specifically, control unit 31 controls lighting unit 36 to turn on and sound generation unit 37 to output the sound during imaging of the preliminary exposure image in the preliminary exposure and imaging of the main image in the main exposure. On the other hand, control unit 31 controls lighting unit 36 to turn off and sound generation unit 37 not to output the sound before imaging of the preliminary exposure image in the preliminary exposure and after imaging of the main image in the main exposure.

Control unit 31, and then, controls lighting unit 36 and sound generation unit 37 to be in the states based on those at the time of imaging between the preliminary exposure and the main exposure by radiation imaging system 100. More specifically, control unit 31 controls lighting unit 36 to turn on and sound generation unit 37 to output the sound during the period from the end of imaging of the preliminary exposure image to the start of imaging of the main exposure image. In other words, between the preliminary exposure and the main exposure, control unit 31 controls the states of lighting unit 36 and sound generation unit 37 to be the same as the state at the time of imaging of the exposure image.

In the manner described above, it is possible to suppress users such as a patient or a radiographer from mistaking the period from the end of imaging of the preliminary exposure image to the start of imaging of the main exposure image for the end of imaging by radiation imaging system 100.

By way of example, similar to a conventional configuration as illustrated in FIG. 5, assuming that lighting unit 36 is turned off, and sound generation unit 37 does not output the sound between the preliminary exposure and the main exposure as in the case after end of imaging of the main exposure image. In this case, when the period from the end of imaging of the preliminary exposure image to the start of imaging of the main exposure image is sufficiently short (e.g., few hundred milliseconds), the period during which lighting unit 36 is turned off and sound generation unit 37 does not output the sound is also sufficiently short. Thus, the user does not recognize that lighting unit 36 turns off and sound generation unit 37 does not output the sound.

However, when a transfer time of the preliminary exposure image or an analyzing time of the preliminary exposure image extend, deriving of an imaging condition of the main exposure is delayed accordingly; and thereby, the period from the end of imaging of the preliminary exposure image to the start of imaging of the main exposure image extends. As a result, the user recognizes that lighting unit 36 turns off and sound generation unit 37 does not output the sound.

Thus, the patient may mistake the end of imaging of the preliminary exposure image for the end of imaging of the main exposure image and may move his body before imaging of the main exposure, which may lead to imaging failures due to body movement of the patient.

In addition, the radiographer may mistake the end of imaging of the preliminary exposure image for the end of imaging of the main exposure image and may stop imaging of the exposure image, which may lead to imaging failures.

By contrast, in the present embodiment, as illustrated in FIG. 4, the states of lighting unit 36 and sound generation unit 37 are controlled to be the same as the state during imaging between the preliminary exposure and the main exposure by radiation imaging system 100. This allows suppressing the user from mistaking the period from the end of imaging of the preliminary exposure image to the start of imaging of the main exposure image for the end of imaging by radiation imaging system 100. As a result, the frequency of imaging failures in radiation imaging system 100 can be reduced.

In the present embodiment, a combined exposure image may be generated by combining the preliminary exposure image and the main exposure image. That is, the above imaging condition may be a condition to combine the preliminary exposure image obtained by the preliminary exposure (the first exposure) and the main exposure (the second exposure).

In this case, a change of geometric arrangement of the subject between the preliminary exposure image and the main exposure image can be reduced by suppressing the mistake of the user (e.g., body movement of the patient). Thus, the above control is effective for the configuration not combining the preliminary exposure image and the main exposure image, and the above control is more particularly effective for the configuration combining the preliminary exposure image and the main exposure image, because it enables more accurate image combining.

Note that, in the above embodiment, lighting unit 36 and sound generation unit 37 are both controlled to be in the states based on these at the time of imaging between the preliminary exposure and the main exposure; however, the present invention is not limited thereto. In one example, control unit 31 may control at least one of lighting unit 36 and sound generation unit 37 to be in the state based on that at the time of imaging.

For example, as illustrated in FIG. 6, control unit 31 may control lighting unit 36 to turn off and sound generation unit 37 to output the sound between the preliminary exposure and the main exposure. Furthermore, as illustrated in FIG. 7, control unit 31 may control lighting unit 36 to turn on and sound generation unit 37 not to output the sound between the preliminary exposure and the main exposure.

Note that, a radiographer may recognize the imaging condition (e.g., the preliminary exposure and the main exposure are performed separately) in radiation imaging system 100 beforehand. In this case, when the transmission unit is controlled to be in the same state during the period from the start of imaging of the preliminary exposure image to the end of imaging of the main exposure image as illustrated in FIG. 4, the radiographer may not be able to distinguish the period of imaging of the preliminary exposure image or the main exposure from the period of non-imaging between the preliminary exposure and the main exposure.

However, performing the control as illustrated in FIG. 6 or 7 allows the radiographer who recognizes beforehand the imaging condition of radiation imaging system 100 to easily distinguish the period of imaging of the preliminary exposure image or the main exposure from the period of non-imaging between the preliminary exposure and the main exposure.

Besides, control unit 31 may turn on lighting unit 36 between the preliminary exposure and the main exposure with difference patterns from those during the preliminary exposure or the main exposure. Furthermore, control unit 31 may set a buzzer sound of sound generation unit 37 between the preliminary exposure and the main exposure differently from that during the preliminary exposure or the main exposure.

For example, a lighting pattern in the lighting unit may include different colours or luminance, and a flushing pattern in the lighting unit may have a plurality of flushing states with different patterns.

In addition, a sound pattern in the sound generation unit, for example, may include a plurality of buzzer sounds or buzzer sounds having different pitches or volume levels.

Thus, the radiographer can easily distinguish the period of imaging of preliminary exposure image or main exposure from the period of non-imaging between preliminary exposure and main exposure.

In the above embodiment, lighting unit 36 and sound generation unit 37 have been illustrated as transmission units; however, the present invention is not limited thereto. For example, as illustrated in FIG. 8, console 3 may include first lighting unit 36A, second lighting unit 36B and sound generation unit 37 as transmission units.

In this case, as illustrated in FIG. 9, control unit 31 controls first lighting unit 36A and second lighting unit 36B to turn on and sound generation unit 37 to output a sound during imaging of a preliminary exposure image in a preliminary exposure and during imaging of a main exposure image in a main exposure. In addition, control unit 31 controls first lighting unit 36A and second lighting unit 36B to turn off and sound generation unit 37 not to output a sound before imaging of the preliminary exposure image in the preliminary exposure and after imaging of the main image in the main exposure.

Control unit 31, then, controls at least one of first lighting unit 36A, second lighting unit 36B, and sound generation unit 37 to be the state based on that at the time of imaging of an exposure image between the preliminary exposure and the main exposure by radiation imaging system 100. In other words, control unit 31 performs control at least one transmission unit (first transmission unit) to be the state based on that at the time of imaging of an exposure image between the preliminary exposure and the main exposure.

Control unit 31 may control the second transmission unit other than the first transmission unit, which has been set to be in the state based on that at the time of imaging of an exposure image, to be in a state different from the state based on that at the time of imaging (i.e., the state of the first transmission unit) between the preliminary exposure and the main exposure by radiation imaging system 100. For example, control unit 31 may turn on either one of first lighting unit 36A or second lighting unit 36B and turn off the other between the preliminary exposure and the main exposure. In FIG. 9, as an example, first lighting unit 36A is turned on, and second lighting unit 36B is turned off.

Thus, the radiographer recognizes that the imaging of the main exposure image has not been ended by seeing first lighting unit 36A being turned on, and recognizes that the exposure is not being executed by seeing second lighting unit 36B being turned off between the preliminary exposure and the main exposure. As a result, the radiographer can easily distinguish the period of imaging of the preliminary exposure image or the main exposure from the period of non-imaging between the preliminary exposure and the main exposure.

Note that, control unit 31 may control first lighting unit 36A and second lighting unit 36B to turn on and sound generation unit 37 to output the sound between the preliminary exposure and the main exposure.

Besides, instead of the lighting unit, a mark indicating a state of the device, such as "exposure in progress" may be displayed on display unit 34 of console 3. Furthermore, as the lighting unit, for example, a lamp to be placed in console 3 or radiation irradiation apparatus 1 may be used. As the sound generation unit, for example, a buzzer to be placed in radiation irradiation apparatus 1 may be used.

Note that, the lamp (transmission unit) to be placed in radiation irradiation apparatus 1 includes, for example, a lamp to be placed in a hand switch, which is used by the user to operate radiation irradiation apparatus 1 (radiation imaging system 100). With respect to the hand switch, the radiographer (the user) tends to recognize that pressing and releasing of the hand switch are directly related to the display of the lamp. Thus, the state of the lamp of the hand switch may be a state based on that at the time of imaging of the exposure image between the preliminary exposure and the main exposure. This enables the radiographer to avoid releasing the hand switch automatically, which reduces the frequency of imaging failures.

Further, control unit 31 is capable of selecting a plurality of transmission patterns, that is, a combination of the states between the preliminary exposure and the main exposure from two or more transmission units and may set one transmission pattern selected from among the plurality of transmission patterns to be a state of the two or more transmission units. For example, control unit 31 may select one transmission pattern based on at least one of the information on the user and the information on an apparatus related to radiation imaging system 100.

For example, some radiographers may be familiar with radiation imaging system 100, and some are unfamiliar. In other words, the degree of proficiency and the degree of familiarity with the system of the radiographer may differ depending on the radiographer.

Some radiation imaging systems 100 may be logged in to be used. Such radiation imaging system 100 has information on the radiographer currently in use; and thus, control unit 31 may appropriately switch the state of the transmission unit for each radiographer, or based on an attribute group of the radiographer (e.g., proficiency, belonging department and imaging frequency).

Furthermore, in some hospitals where radiation imaging system 100 is installed, an inexperienced radiographer may frequently use a particular imaging room or an imaging apparatus in the imaging room. In addition, some hospitals may assign an inexperienced radiographer to a nursing cart for hospital wards. In such a case, control unit 31 may appropriately switch the state of the transmission unit according to the attribute of the apparatus to be used.

For example, when the proficiency of the radiographer is relatively low or the inexperienced radiographer uses the apparatus, control unit 31 selects a transmission pattern according to the state of FIG. 4. On the other hand, when the proficiency of the radiographer is relatively high or the experienced radiographer uses the apparatus, control unit 31 selects a transmission pattern according to the state of FIG. 6 or 7.

The information on the user or the apparatus may be provided selectably in display unit 34 and operation unit 35.

Consequently, a transmission pattern capable of more accurately transmitting the operation state of the radiation imaging system is made available for the radiographer (the user) familiar with the imaging or the operation of apparatus, which makes it easier for the user to understand the operation state, and thus, the frequency of imaging failures can be reduced. On the other hand, a simple transmission pattern is available for the radiographer unfamiliar with the imaging or the operation of apparatus, which enables to suppress the user from mistaking the period from the end of imaging of the preliminary exposure image to the start of imaging of the main exposure image for the end of imaging in radiation imaging system 100, and thus, the frequency of imaging failures can be reduced.

Besides, some apparatuses according to the radiation imaging system once open exposure switch 12 between the preliminary exposure and the main exposure, while others do not open exposure switch 12 between the preliminary exposure and the main exposure.

For example, with the apparatus that once opens exposure switch 12 between the preliminary exposure and the main exposure, the radiographer intentionally performs an operation of opening exposure switch 12; thus, the radiographer may easily recognize the state of imaging when the state of the transmission unit is changed in response to the operation. In this case, control unit 31, for example, selects the transmission pattern according to the state illustrated in FIG. 9 in the configuration illustrated in FIG. 8 to set the states of the first lighting unit 36A and the second lighting unit 36B are to be different from each other.

Also, in the apparatus that does not open exposure switch 12 between the preliminary exposure and the main exposure, the radiographer does not intentionally operate exposure switch 12 between the preliminary exposure and the main exposure. Therefore, the radiographer may easily recognize the state of imaging when the state of the transmission unit is not changed between the preliminary exposure and the main exposure.

In this case, control unit 31 may, for example, select the transmission pattern according to the state illustrated in FIG. 4 in the configuration illustrated in FIG. 3 so that the state of the transmission unit does not change from the start of imaging of the preliminary exposure image to the end of imaging of the main exposure image.

Thus, using the transmission pattern in accordance with the operation to be performed by the radiographer enables the radiographer (user) to intuitively understand the state of radiation imaging system 100, which improves the usability of the radiographer.

Note that, it is possible to allow setting either one of the apparatus that once opens exposure switch 12 between the preliminary exposure and the main exposure and the apparatus that does not open exposure switch 12 between the preliminary exposure and the main exposure. Then, control unit 31 may switch the state of the transmission unit based on the setting. Thus, the difference due to the type and operation state of the apparatus can be absorbed, which allows coping with a plurality of apparatuses using a common system.

Figure 10:
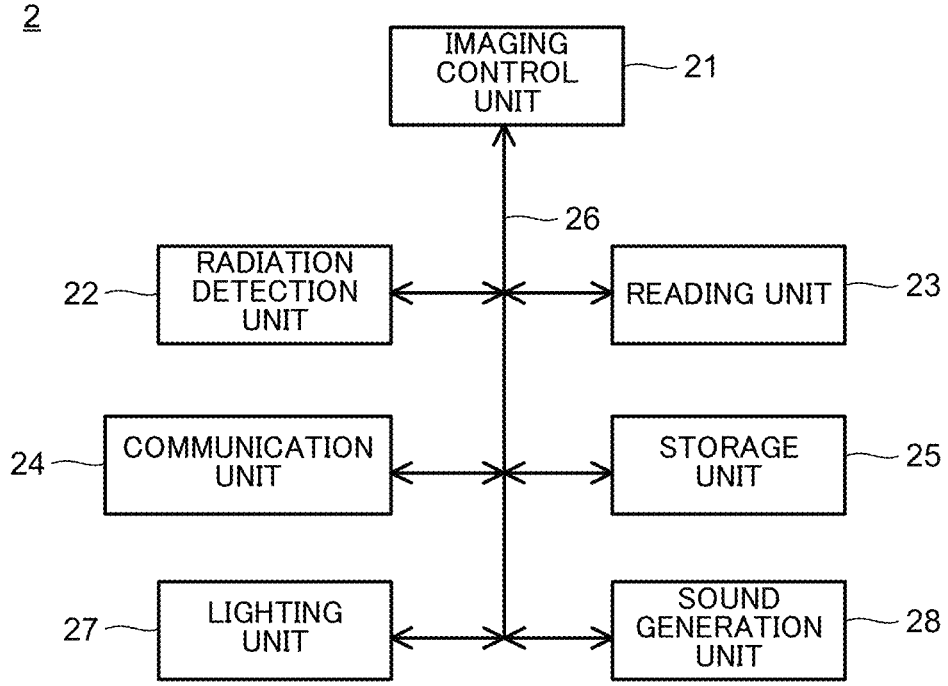
FIG. 10 is a block diagram of a specific configuration of a radiation irradiation apparatus according to a variation.

In the above embodiment, the transmission unit is installed in the console; however, the present invention is not limited thereto. As illustrated in FIG. 10, the transmission unit, for example, may be installed in radiation imaging apparatus 2. Radiation imaging apparatus 2 illustrated in FIG. 10 corresponds to the "transmission apparatus" of the present invention.

Radiation imaging apparatus 2 in this configuration includes lighting unit 27 and sound generation unit 28 in addition to the configuration of FIG. 2. Lighting unit 27 and sound generation unit 28 mainly transmits the operation state of the radiation imaging system to the patient under the control of imaging control unit 21.

Such a configuration is applicable, for example, to a radiation imaging system in which an imaging room that has radiation irradiation apparatus 1 and radiation imaging apparatus 2 and an operation room that has console 3 are separately arranged.

As illustrated in FIG. 11, imaging control unit 21 controls lighting unit 27 to turn on and sound generation unit 28 to output the sound based on the control signal of console 3 or the like between the preliminary exposure and the main exposure. This enables to suppress the patient from mistaking the end of the preliminary exposure for that of the main exposure.

Further, sound generation unit 28 may output a sound such as voice guidance to the patient instead of the buzzer sound. For example, sound generation unit 28 outputs the sound of "Take a breath and hold it" when preparing for imaging at the time of imaging a preliminary exposure image. Then, sound generation unit 28 outputs a sound of "Stop breathing" when the imaging of the preliminary exposure image is started. Furthermore, sound generation unit 28 outputs a sound of "please relax" when the imaging of the main exposure image is ended. This allows accurately transmitting to the patient that the exposure image is in progress. Further, a character display such as the above-described voice guidance may be performed by using a display unit as the transmission unit. In such a configuration, although sound generation unit 28 of radiation imaging apparatus 2 may be incorporated in radiation imaging apparatus 2, sound generation unit 28 may also be configured with a speaker connected by wire or wirelessly to radiation imaging apparatus 2 and be placed in a location from where the voice easily reaches to the patient. Thus, the radiographer can transmit instructions to the patient via the speaker, which makes it easier for the patient to perform the action required for imaging. Similarly, the display unit may be connected to radiation imaging apparatus 2 by wire or wirelessly, be configured with an indicator to be communicated, and be placed in a location where the patient can easily make visual recognition. This makes it easier for the patient to perform the action required for imaging by checking the indicator.

The above speaker and the indicator may be connected to the console or the radiation irradiation apparatus by wire or wirelessly.

Further, the lighting unit and the sound generation unit of console 3 in the radiation imaging system to which the radiation imaging apparatus 2 is applied functions mainly as a transmission unit that transmits the operation state of the radiation imaging system to the radiographer.

For example, as illustrated in FIG. 12, in the configuration in which console 3 has first lighting unit 36A and second lighting unit 36B, control unit 31 may control first lighting unit 36A to turn on, second lighting unit 36B to turn off, and generation unit 37 not to output the sound between the preliminary exposure and the main exposure.

This enables the radiographer to recognize both a series of imaging of the preliminary exposure image and the main exposure image is continued and the period when the exposure is performed among the series of imaging via first lighting unit 36A being turned on. As a result, the operation state of the radiation imaging system can be easily understood, which reduces the frequency of imaging failures.

In addition, changing the lighting pattern of the lighting unit and the sound pattern of the sound generation unit in the console side in such a configuration between the exposure time and the non-exposure time during of imaging the exposure image enables the radiographer to accurately understand the periods. That is, control unit 31 sets the states of the transmission unit to be different between the exposure time and the non-exposure time during of imaging the exposure image.

For example, in an example illustrated in FIG. 12, second lighting unit 36B is turned off, and sound generation unit 37 does not output the sound in the period during non-exposure at the time of imaging preparation of the preliminary exposure image and the main exposure image. In the period during imaging of the preliminary exposure image and the main exposure image (during the exposure), second lighting unit 36B is turned on, and sound generation unit 37 outputs sound. On the other hand, first lighting unit 36A is turned on in both the period during non-exposure at the time of imaging preparation of the preliminary exposure image and the main exposure image and the period during imaging of the preliminary exposure image and the main exposure image.

This enables the radiographer to accurately recognize the period during the exposure and the period during the non-exposure in imaging of the exposure image. As a result, the frequency of imaging failures in the radiation imaging system due to misrecognition of the periods by the user can be reduced.

Further, providing both the lighting unit and the sound generation unit as the transmission unit of the radiation imaging apparatus enables providing a radiation imaging system corresponding to both a patient having a visual impairment and a patient having a hearing impairment.

For the patient having only the visual impairment, the sound generation unit is sufficient in the radiation imaging system, and the lighting unit is not always necessary. On the other hand, for the patient having only the hearing impairment, the lighting unit is sufficient in the radiation imaging system, and the sound generation unit is not always necessary.

Meanwhile, when having both the hearing impairment and the visual impairment, the patient may not be able to recognize a lighting of the lighting unit or a sound of the sound generation unit. Hence, a device acting on a tactile sense of the user may be applied as the transmission unit.

Such devices include, for example, a device having a vibrating function that can be held by the patient (e.g., a portable terminal such as mobile phone and smartphone or an watch-type electronic device).

For example, the above-described device vibrates by communicating the device with console 3 and outputting a command to instruct the device to vibrate from console 3 during the period from the start of imaging of the preliminary exposure image to the end of imaging of the main exposure image. Moreover, a command to stop the vibration of the device is output from console 3 before the start of imaging of the preliminary exposure image or after the end of imaging of the main exposure image.

This allows the user having visual and hearing impairments to recognize an operation state of the radiation imaging system, which reduces the frequency of imaging failures in the radiation imaging system.

Further, the transmission unit suitable for the patient may be selected based on patient information. In this case, for example, display unit 34 and operation unit 35 of console 3 may be provided in such a manner that allows the patient information to be selected. Besides, console 3 may automatically select the patient information based on the patient information obtained from, for example, RIS.

In the above embodiment, transmission pattern is the same in the preliminary exposure and the main exposure (the pattern for turning on of lighting unit 36, and the pattern for outputting the sound of sound generation unit 37); however, the present invention is not limited thereto. For example, the transmission pattern may be different in the preliminary exposure and in the main exposure. In this case, the transmission pattern between the preliminary exposure and the main exposure may be the same as that of either one of the preliminary exposure or the main exposure. This enables the radiographer to recognize whether the preliminary exposure or the main exposure is in progress. The main exposure is performed at the dose higher than that for the preliminary exposure; thus stopping the main exposure in the way of imaging to perform re-exposure is not undesirable because the total exposure dose of the patient increases. Recognizing whether the preliminary exposure or the main exposure is in progress enables the radiographer to determine whether or not to suspend the exposure, taking into account a trade-off relation between the magnitude of the possibility of imaging failures (e.g., the magnitude of body movement) and the total exposure dose by re-exposure, which consequently reduces the exposure dose of the patient.

In the above embodiment, the transmission control apparatus is a control unit of the console installed in the radiation imaging system; however, the present invention is not limited thereto. For example, the transmission control apparatus may be an external apparatus installed in a place different from the radiation imaging system. In this case, the transmission control apparatus, for example, outputs the determined state of the transmission unit to the radiation imaging system by radio communication or the like.

In the above embodiment, radiation imaging system 100 has an automatic exposure control function; however, the present invention is not limited thereto. Radiation imaging system 100 may have any control function as far as having the configuration for imaging the exposure image by exposures including the first exposure and the second exposure.

In the above-described embodiment, as the control in which the state of the transmission unit is set to be the state at the time of imaging of the exposure image, the state of one or more transmission units is the same as the state at the time of imaging of the exposure image; however the present invention is not limited thereto. The state of one or more transmission units may not be the same as the state at the time of imaging the exposure image unless the user erroneously recognizes the state of the transmission unit; for example, the state may be similar to the state at the time of imaging the exposure image.

In the above embodiment, the control unit in the transmission apparatus is configured integrally with the storage unit, the display unit, the operation unit, and the like; however the present invention is not limited thereto. The control unit may be configured separately from the storage unit, the display unit, the operation unit, and the like. For example, the control unit may be installed in the radiation irradiation apparatus. That is, when the transmission unit is installed in the radiation irradiation apparatus, the transmission unit and the control unit are to be installed in the radiation irradiation apparatus. Further, the control unit may be installed in the radiation irradiation apparatus. In the case where the transmission unit is installed in the radiation irradiation apparatus, the transmission unit and the control unit is not to be installed in the console. In other words, the transmission unit is installed in the radiation irradiation apparatus, and the control unit is installed in the radiation imaging apparatus.

The above embodiment has a configuration in which one main exposure is performed after one preliminary exposure, but the present invention is not limited thereto. A configuration in which a plurality of main exposures are performed after one preliminary exposure is also possible. In this configuration, control unit 31 performs an automatic exposure control to decide the imaging conditions for the plurality of main exposure based on a preliminary exposure image obtained in the preliminary exposure and the incidental information associated with the preliminary exposure image.

Figure 13:
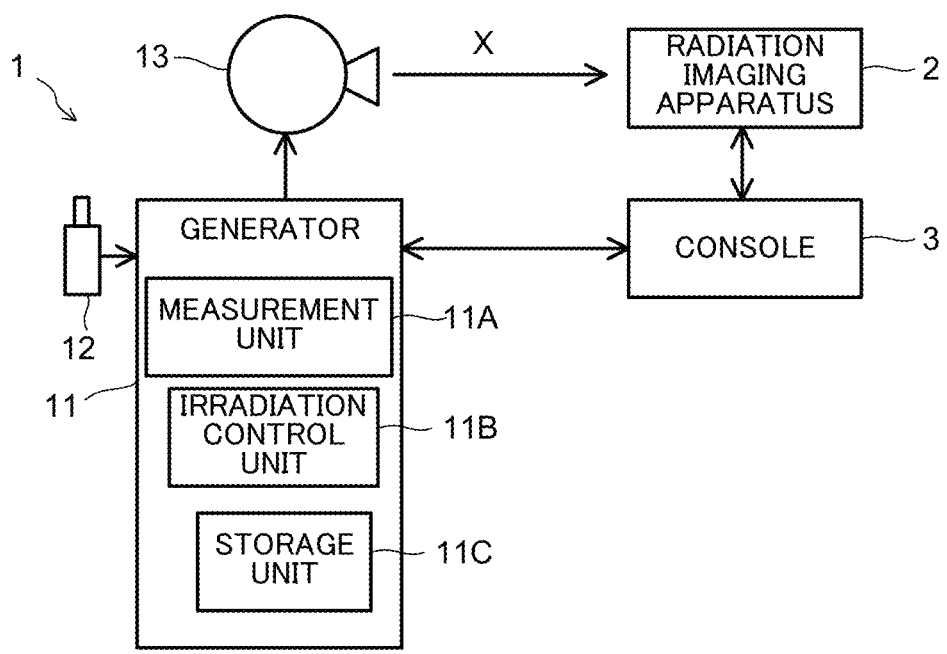
FIG. 13 is a block diagram of a configuration of a radiation imaging system according to a second embodiment of the present invention.

Hereinafter, a second embodiment of the present invention will be described with reference to the drawings. FIG. 13 is a block diagram of a configuration of radiation imaging system 100 according to the second embodiment of the present invention.

As illustrated in FIG. 13, radiation imaging system 100 according to the present embodiment is configured to include radiation irradiation apparatus 1, radiation imaging apparatus 2, and console 3. Further, radiation imaging system 100 is connectable to, for example, Radiology Information System (RIS) and Picture Archiving and Communication System (PACS) and/or the like (not illustrated).

Radiation irradiation apparatus 1 is connected to console 3 so as to be able to communicate thereto by wire or wirelessly. Further, radiation irradiation apparatus 1 is configured to include generator 11, exposure switch 12 and radiation source 13.

Generator 11 is capable of applying a voltage in accordance with preset radiation exposure conditions (for example, tube voltage, tube current, irradiation time, product of tube current and time (mAs-value)—hereinafter also referred to as "tube current time product")—to radiation source 13, based on the operation of exposure switch 12.

Further, generator 11 includes measurement unit 11A, irradiation control unit 11B, and storage unit 11C. Measurement unit 11A measures a time (a derivation time) indicating a derivation completion timing for deriving the main exposure condition of the main exposure based on the preliminary exposure image by preliminary exposure in the automatic exposure control to be described below. The derivation time includes all the time required for necessary processing before the main exposure condition can be set in generator 11. For example, a communication time for transmitting the main exposure conditions based on the preliminary exposure image from console 3 to be described below to generator 11 is also included.

Note that, measurement unit 11A may be an up-counter that starts counting at the timing of the measurement start and stops or resets counting at the timing of the measurement end, or a down-counter, or may calculate an elapsed time by measuring itself the current time. The configuration that measures the current time eliminates the need for additionally installing a device such as a counter, thus, making it possible to achieve a smaller and more inexpensive device.

Irradiation control unit 11B includes, for example, Central Processing unit (CPU), Random Access Memory (RAM), or the like. The CPU of irradiation control unit 11B reads out various programs stored in storage unit 11C, loads the programs into the RAM, performs various kinds of processing according to the loaded programs, and centrally controls operations of respective units of radiation irradiation apparatus 1 based on reception, for example, a control signal from the external device such as console 3.

When succeeding in receiving exposure condition from console 3 before the end of the time measurement by measurement unit 11A, irradiation control unit 11B sets the received exposure condition. When failing to receive the exposure condition, irradiation control unit 11B sets preliminary exposure conditions to be described below. Irradiation control unit 11B corresponds to the processing device of the present invention.

Radiation source 13 (tube bulb) includes a rotating anode and a filament and the like (not illustrated). When generator 11 applies a voltage, the filament irradiates the rotating anode with an electron beam corresponding to the applied voltage, and the rotating anode then generates radiation X (for example, X-ray) with a dose corresponding to the intensity of the electron beam.

FIG. 13 illustrates an example including separated generator 11, exposure switch 12 and radiation source 13, but the components may be integrally configured. FIG. 1 illustrates an example including exposure switch 12 connected to generator 11, but exposure switch 12 may be provided in another apparatus. Radiation irradiation apparatus 1 may be installed in an imaging room, or may be configured to be movable by being incorporated in a nursing cart for examination or the like.

Radiation imaging apparatus 2 is connected to console 3 so as to be able to communicate thereto by wire or wirelessly. Radiation imaging apparatus 2 is configured such that it can generate image data of an exposure image of a subject by receiving radiation X exposure through the subject from radiation irradiation apparatus 1.

Figure 14:
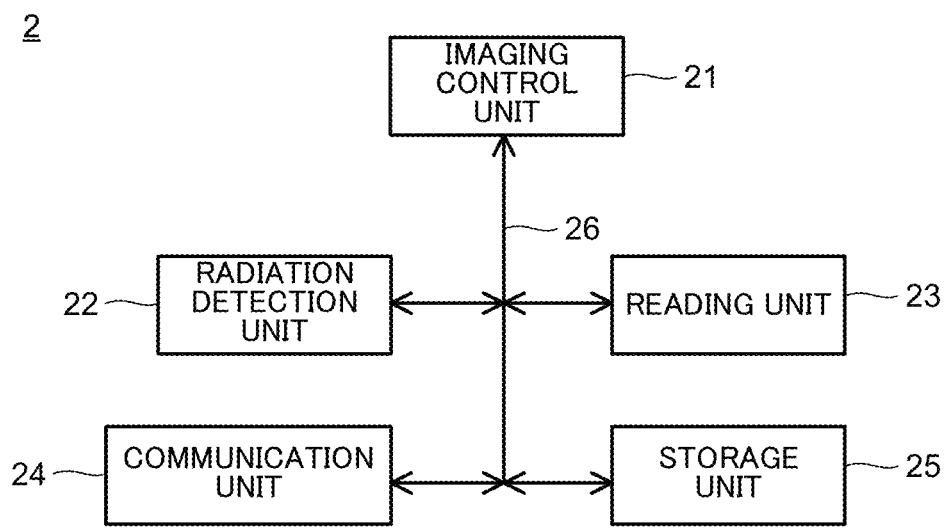
FIG. 14 is a block diagram of the specific configuration of the radiation irradiation apparatus.

As illustrated in FIG. 14, radiation imaging apparatus 2 includes imaging control unit 21, radiation detection unit 22, reading unit 23, communication unit 24, storage unit 25, and bus 26 connecting each unit.

Imaging control unit 21 includes a central processing unit (CPU), a random access memory (RAM), and the like. The CPU of imaging control unit 21 reads various programs stored in storage unit 25, loads the programs in the RAM, executes various kinds of processing according to the loaded programs, and centrally controls the behavior of each unit in the radiation imaging apparatus 2 based on a control signal or the like received from an external apparatus such as console 3.

Radiation detection unit 22 includes a substrate in which pixels equipped with a switch element and a radiation detection element generating electric charge according to a dose by receiving radiation X are arranged in a two-dimensional shape (matrix shape).

Reading unit 23 is capable of reading the amount of the electric charge discharged from each pixel as a signal value, and generating image data from a plurality of signal values.

Communication unit 24 is capable of receiving various control signals, various kinds of data and the like from an external apparatus, and transmitting various control signals, generated image data and the like to the external apparatus.

Storage unit 25 includes a nonvolatile semiconductor memory, a hard disk and the like, and stores various programs to be executed by imaging control unit 21, parameters necessary for the execution of the programs, and the like. Storage unit 25 is also capable of storing image data generated by reading unit 23 and various kinds of data processed by imaging control unit 21.

With imaging control unit 21 turning off the switch elements of radiation detection unit 22, radiation imaging apparatus 2 having the above described configuration accumulates electric charge in each pixel according to the radiation dose upon receiving radiation exposure. When imaging control unit 21 turns on each switch element and the electric charge is discharged from each pixel, reading unit 23 converts each electric charge amount into a signal value and reads it out as image data.

Radiation imaging apparatus 2 may have a configuration such that a scintillator or the like is incorporated, the scintillator converts emitted radiation X into light with another wavelength such as visible light, and electric charge according to the converted light is generated, or a configuration such that the electric charge is directly generated from radiation X without passing through the scintillator or the like. Radiation imaging apparatus 2 may be a dedicated machine type integrated with an imaging table, or a portable type.

Console 3 includes a PC, a portable terminal or a dedicated apparatus, and is connected to, for example, radiation irradiation apparatus 1 and radiation imaging apparatus 2 so as to be able to communicate thereto by wire or wirelessly. Console 3 can set, for example, the imaging conditions of radiation irradiation apparatus 1 and radiation imaging apparatus 2, the imaging target area, and the like based on the imaging order from an external apparatus (RIS or the like) or the operation from a user.

Figure 15:
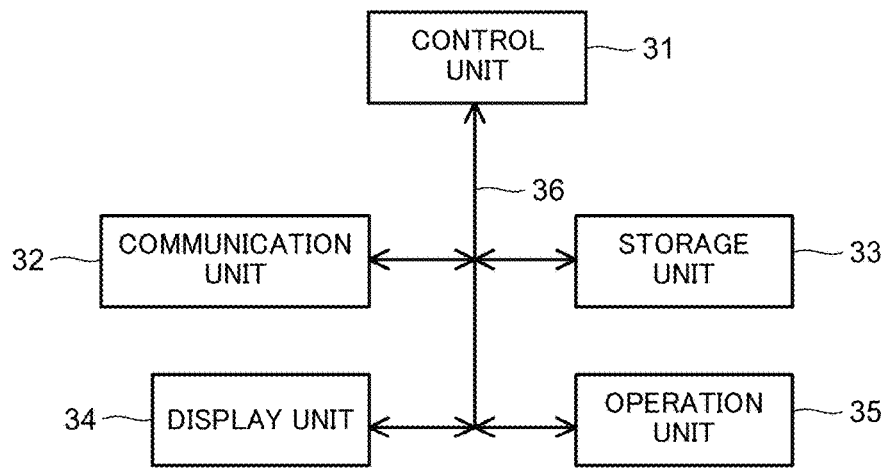
FIG. 15 is a block diagram of a specific configuration of a console.

As illustrated in FIG. 15, console 3 includes control unit 31, communication unit 32, storage unit 33, display unit 34, operation unit 35, and bus 36 connecting each unit.

Control unit 31 includes a CPU, a RAM and the like. The CPU of control unit 31 reads various programs stored in storage unit 33 according to the operation from operation unit 35, loads the programs in the RAM, executes various kinds of processing according to the loaded programs, and centrally controls the behavior of respective units of console 3.

Communication unit 32 includes a LAN adapter, a modem, a terminal adapter (TA) and the like, and controls data transmission and reception with each apparatus connected to a communication network.

Storage unit 33 includes a nonvolatile semiconductor memory, a hard disk and the like, and stores various programs to be executed by control unit 31, parameters necessary for the execution of the programs, and the like. Further, storage unit 33 can store the image data received from radiation imaging apparatus 2 and the image data processed by control unit 31 so that the image date associates with the incidental information.

Display unit 34 includes a monitor such as Liquid Crystal Display (LCD) or Cathode Ray Tube (CRT) and displays input instruction, data and the like from operation unit 35 according to the instruction of a display signal input from control unit 31.

Operation unit 35 is configured to include a keyboard provided with cursor keys, numeric input keys, various function keys and the like, and a pointing device such as a mouse. Operation unit 35 outputs an instruction signal input by a key operation via the keyboard or a mouse operation to control unit 31. Operation unit 35 may be provided with a touch panel on the display screen of display unit 34, and, in this case, operation unit 35 outputs an instruction signal input through the touch panel to control unit 31.

Next, the control of radiation imaging system 100 by irradiation control unit 11B and control unit 31 will be described. Irradiation control unit 11B and control unit 31 perform automatic exposure control to determine main exposure condition for performing the main exposure based on the preliminary exposure image obtained by the preliminary exposure and the incidental information related to the preliminary exposure image. The preliminary exposure is performed prior to the main exposure at a dose lower than the dose of the main exposure.

In the automatic exposure control, imaged preliminary exposure image is transferred between radiation imaging apparatus 2 and console 3, and the preliminary exposure image is image analyzed in console 3. Console 3 derives the main exposure condition of the main exposure by image analyzing of the preliminary exposure image.

Figure 16:
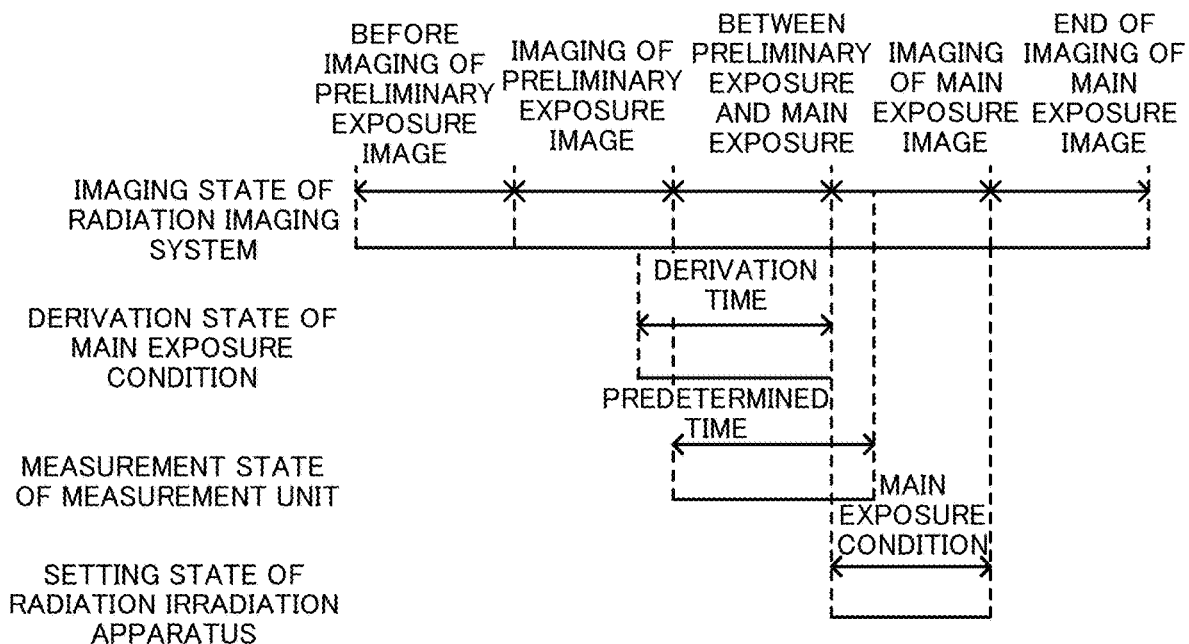
FIG. 16 illustrates an exemplary time change of a radiation imaging system, a main exposure condition, a measurement unit, and each state in a radiation irradiation apparatus.
Figure 17:
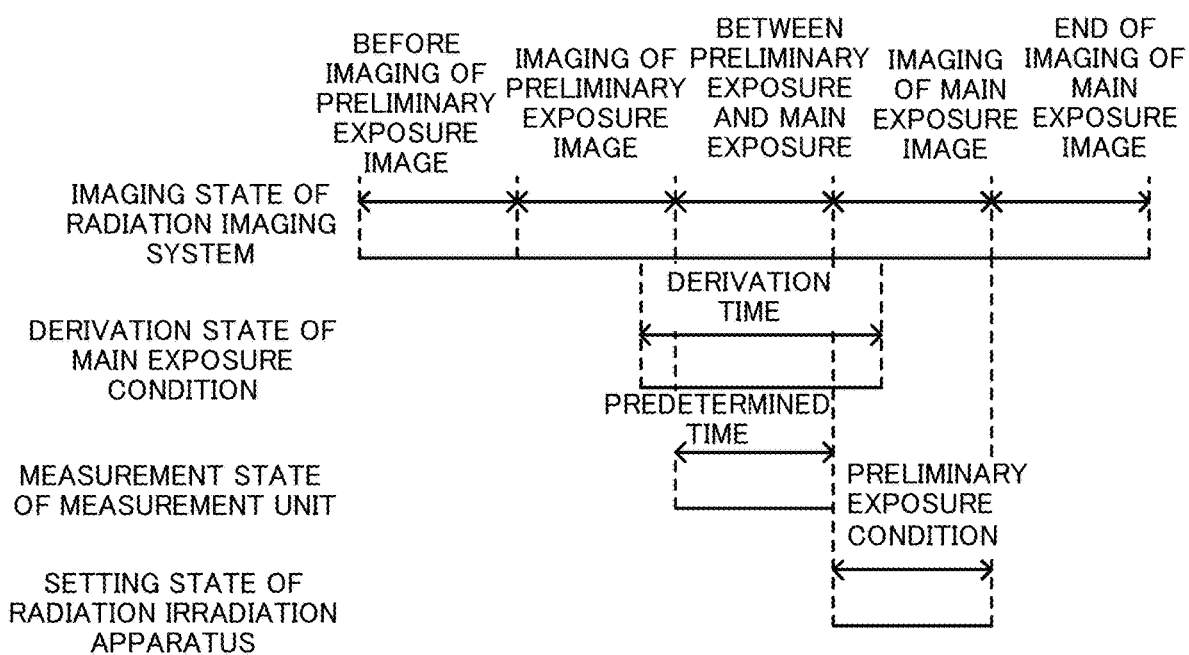
FIG. 17 illustrates an exemplary time change of each state in the radiation imaging system, the main exposure condition, the measurement unit, and the radiation irradiation apparatus.

For example, as illustrated in FIG. 16, the preliminary exposure image is transferred to console 3 while the imaging of the preliminary exposure image by radiation imaging system 100 is in progress, and console 3 starts deriving the main exposure condition of the main exposure. Note that, for example, FIGS. 16 and 17 illustrates time variation of the imaging state of radiation imaging system 100, the derivation state of the main exposure condition by control unit 31, the measurement state of measurement unit 11A, and the setting state of radiation irradiation apparatus 1.

Irradiation control unit 11B receives from the console 3 the main exposure condition of the main exposure derived based on the preliminary exposure in console 3 and determines whether the main exposure condition can be used. Then, irradiation control unit 11B, according to the determination result of the use of the main exposure condition, performs change processing of the execution mode of the main exposure. Irradiation control unit 11B corresponds to the determination unit and the processing unit of the present invention.

Specifically, irradiation control unit 11B determines that the main exposure condition can be used in a case where a reception timing of the main exposure condition is obtained before the measurement time of measurement unit 11A reaches a predetermined time.

The predetermined time means the maximum time that may be taken from the end of imaging of the preliminary exposure image to the start of imaging of the main exposure image. In other words, the predetermined time specifies the limit value of the delay in starting of the main exposure that has no influence on the success or failure of imaging. Therefore, the value considering the success or failure of imaging is set. For example, the following relation is found beforehand by an experiment and set as a predetermined time in generator 11; the relation among the magnitude of body movement during imaging, the time from the end of imaging of the preliminary exposure image to the start of imaging of the present exposure image, and whether the finally obtained image can achieve the purpose of imaging. Since this relation varies depending on the imaging area, the attributes of the patient, the purpose of imaging, and the like, setting an optimal predetermined time for each type or each type of group is preferable, which will be described below. Alternatively, a predetermined time encompassing all types may be set instead of changing the value for each type or each type of group. In this case, the shortest predetermined time is set among predetermined times of all types. In addition, such setting can be achieved with a small amount of memory because the number of values to be set as a predetermined time is small, which enables suppressing equipment costs.

The predetermined time is set to generator 11, for example, by transmitting a value input by the user from operation unit 35 of console 3 to generator 11 via communication unit 32 and storing the value in storage unit 11C of generator 11. In a case where generator 11 has an operation unit, the value input by the user from the operation unit may be stored in storage unit 11C.

Measurement unit 11A starts measurement of the elapsed time from the end of imaging of the preliminary exposure image and ends the measurement after the predetermined time has elapsed.

Irradiation control unit 11B, for example, determines whether the main exposure condition has been derived before the predetermined time elapses by using the state of whether the time measurement obtained from measurement unit 11A of generator 11 has ended and the state of whether generator 11 has received the main exposure condition (i.e., the state of whether the main exposure derivation has ended). Note that, the determination method is not limited thereto; for example, whether the main exposure condition has been derived before the predetermined time elapses may be determined by comparing the measurement time and the predetermined time at the time of reception.

Irradiation control unit 11B determines that the main exposure condition can be used when the derivation of the main exposure condition is completed before a predetermined time elapses. Specifically, irradiation control unit 11B determines that the main exposure condition can be used when receiving the main exposure condition before the time measurement of measurement unit 11A ends (i.e., before the elapsed time from the end of imaging of the preliminary exposure image reaches the predetermined time). Then, the main exposure is immediately started with the main exposure condition after receiving the main exposure condition. That is, the main exposure is started without waiting for the end of the time measurement of measurement unit 11A. This allows performing the main exposure with the small delay as much as possible, using the main exposure condition derived based on the preliminary exposure image. Note that, in a case where necessary preparation to perform the main exposure has not been completed at the time of receiving the main exposure condition, (e.g., the preparation of the tube bulb has not been completed), the main exposure is started after these preparations are ended. When these preparations need to be started after receiving the main exposure condition, the time T required for these preparations needs to be taken into consideration for setting the predetermined time. Specifically, a predetermined time used in measurement unit 11A is set by subtracting the time T from the predetermined time obtained beforehand by the experiment described above. Thereby, the time required between the end of imaging of the preliminary exposure image and the start of imaging of the main exposure image falls within a predetermined time determined by the experiment, which enables preventing imaging failures due to body movement.

Further, as illustrated in FIG. 17, irradiation control unit 11B determines that the main exposure condition cannot be used when the derivation of the main exposure condition is not ended before the predetermined time elapses. Specifically, when not receiving the main exposure condition before the time measurement of measurement unit 11A ends (i.e., before the elapsed time from the end of imaging of the preliminary exposure image reaches the predetermined time), irradiation control unit 11B determines that the main exposure condition cannot be used.

When determining that the main exposure condition cannot be used, irradiation control unit 11B starts the main exposure, using the preliminary exposure condition to be described later and stored in storage unit 11C as the main exposure. That is, the main exposure is imaged with the preliminary exposure condition at the timing of the reaching the predetermined time.

The preliminary exposure condition is determined, for example, based on the imaging area and the imaging direction of the subject in radiation imaging system 100 and determined to be the same as the condition in exposure control other than the automatic exposure control described above in radiation imaging system 100.

The exposure conditions other than the automatic exposure control are, for example, exposure conditions in the imaging of the exposure image by one exposure. The exposure conditions other than the automatic exposure control are, for example, described in a table in association with each combination of the imaging area of the subject (e.g., chest, stomach, head) and the imaging direction (e.g., front, side). This table is stored in storage unit 33 or the like.

When obtaining input information on the imaging area and the imaging direction of the subject, control unit 31 selects the preliminary exposure condition for the combination of the imaging area and the imaging direction based on the input information, referring to the above table. Then, control unit 31 sets the selected preliminary exposure condition to radiation irradiation apparatus 1 (generator 11). Irradiation control unit 11B stores the received preliminary exposure condition in storage unit 11C.

In the present embodiment, the preliminary exposure condition is determined based on the imaging area and the imaging direction; however is not limited thereto as far as the condition affects exposure condition. For example, the exposure condition is affected by body pressure of the patient, body shape of the patient, distance between focal image receiving apparatuses, distance between focal skins, presence/absence and type of additional filters, presence/absence and type of scattered ray removal grids. Therefore, values for each of these combinations may be provided in the tables and then used with reference to the values of the tables based on information with which condition to be set in kymography.

Accordingly, the main exposure is started with the preliminary exposure condition. A start timing of the main exposure in a case of using the main exposure condition derived based on the preliminary exposure image as the imaging condition of the main exposure is a timing of derivation end of the main exposure; however, the timing is earlier than a timing at which a predetermined time elapses from the end of the preliminary exposure. On the other hand, a start timing of the main exposure in a case of using the preliminary exposure condition as the imaging condition of the main exposure is the timing at which a predetermined time elapses from the end of the preliminary exposure. In other words, the start timing of the main exposure in the present embodiment is the earlier timing of: a timing of derivation end of the main exposure, or the timing at which the predetermined time elapses from predetermined time regarding the preliminary exposure. That is, in the present embodiment, regardless of a derivation time of the main exposure condition of the main exposure based on the preliminary exposure image, the main exposure is surely started by a specific time.

Further, in the present embodiment, the main exposure derived based on the preliminary exposure image is determined to be unavailable in a case where, among the timing of derivation end of the main exposure condition and the timing at which the predetermined time elapses from predetermined time regarding the preliminary exposure, the latter is set as the start timing of the main exposure.

A description will be given of problems to be solved by surely starting the main exposure by the specific time regardless of the derivation time of the exposure condition of the main exposure based on the preliminary exposure image. For example, the longer the transfer time of the preliminary exposure image or the image analyzing time of the preliminary exposure image are, the longer the derivation time of the main exposure condition of the main exposure is. This deteriorates usability in the radiation imaging system; for example, the main exposure cannot be started at a specific time.

Further, as the time between the preliminary exposure and the main exposure extends, body movement of the subject increases, and thus, positioning of the subject in the main exposure becomes inappropriate, which may lead to imaging failures.

However, in the present embodiment, when the derivation time of the main exposure condition extends, the main exposure is started in the preliminary exposure condition. Consequently, the main exposure is surely started by the specific time, which enables suppressing the extension of the time between the preliminary exposure and the main exposure.

This reduces the increase in the body movement of the subject caused by the extension of the time between the preliminary exposure and the main exposure, and thus, also reduces the frequency of imaging failures in the radiation imaging system.

Exposure conditions in the exposure control other than the automatic exposure control, for example, are stored in storage unit 33 or the like in a state described in the table in association with the imaging region and the imaging direction. Control unit 31 determines the preliminary exposure condition by referring to this table.

In this manner, the need to separately store the table in which the preliminary exposure condition is described in storage unit 33 is eliminated, and thus, the storage size in storage unit 33 is reduced, which can reduce a cost in the entire apparatus. Note that, the preliminary exposure condition may be corrected after reference to the above table, using the ratio between the imaging distance serving as a prerequisite of the reference value (e.g., the distance of the subject and the radiation irradiation apparatus) and the imaging distance in the actual apparatus.

Further, control unit 31 may determine the preliminary exposure condition so that the dose is lower than that with the conditions in the exposure control other than the automatic exposure control. The exposure control other than the automatic exposure control is a control by one exposure; therefore, when the preliminary exposure condition is set to be the same as the exposure control, the dose of the preliminary exposure condition may be the sum of the dose of the preliminary exposure and the dose of the main exposure.

Therefore, in a configuration adding the preliminary exposure image based on the preliminary exposure and the main exposure image based on the main exposure in the automatic exposure control, assuming that the preliminary exposure condition is set to be the same condition as the exposure control, this is substantially equal to performing the preliminary exposure twice and the main exposure once. As a result, the preliminary exposure will be performed one extra time, which causes an extra exposure of the subject accordingly.

Thus, in the configuration, control unit 31 determines the preliminary exposure condition with a dose obtained by subtracting the dose of the preliminary exposure with respect to the exposure conditions in the exposure control other than the automatic exposure control.

For example, it is assumed that in the exposure conditions in the exposure control other than the automatic exposure control, a tube voltage is 120 kV, a tube current time product is 10 mAs, and in the exposure conditions in the preliminary exposure, a tube voltage is 120 kV, and a tube current time product is 1 mAs.

In this case, in the preliminary exposure condition, the tube voltage is set to 120 kV, the tube current time product is set to 9 mAs by subtracting 1 mAs from 10 mAs. This enables suppressing the extra exposure caused by performing one extra preliminary exposure.

In addition, control unit 31 performs control to display the preliminary exposure condition on display unit 34. For example, in a configuration in which the preliminary exposure and the main exposure are performed by one pressing of exposure switch 12, display unit 34 displays the preliminary exposure condition before the preliminary exposure is performed. In this configuration, since a series of imaging of preliminary exposure and main exposure is performed automatically and in a short time by one pressing operation, the user cannot respond to a value of the pre-imaging condition when the pre-imaging condition is displayed for the first time between the preliminary exposure and the main exposure. Thereby, displaying the preliminary exposure condition before the preliminary exposure enables the user to respond to the value of the pre-imaging condition (e.g., to perform imaging after reviewing the pre-imaging condition when the value of the pre-imaging condition is too large) and to perform imaging with more appropriate imaging conditions.

Further, in the configuration adding the preliminary exposure image based on the preliminary exposure and the main exposure image based on the main exposure and using a common value for the tube voltage and the tube current of the preliminary exposure and the tube voltage and the tube current of the main exposure, the common tube voltage and the common tube current may be displayed together before the preliminary exposure is performed. Furthermore, the irradiation time obtained by summing the irradiation time of the preliminary exposure and the irradiation time of the preliminary exposure condition may be displayed. Besides, tube current time product obtained by summing the common tube voltage, the tube current time product of the preliminary exposure, and the tube current time product of the preliminary exposure condition may be displayed. This enables the user to understand the total radiation output in a series of imaging of the preliminary exposure and the main exposure at a glance, and thus, the usability is improved.

In addition, since irradiation control unit 11B determines to use the preliminary exposure condition, irradiation control unit 11B notifies console 3 that the preliminary exposure condition is used. Thus, display in display unit 34 of console 3 is switched.

In a configuration in which exposure switch 12 is pressed for each of the preliminary exposure and the main exposure, display unit 34 varies display contents of the preliminary exposure condition before and after use of the preliminary exposure condition is determined. Specifically, display unit 34 does not display the preliminary exposure condition until use of the preliminary exposure condition is determined, and displays the preliminary exposure condition after the use of the preliminary exposure condition is determined. Alternatively, the preliminary exposure condition may be displayed in a changed display colour. Until the preliminary exposure condition is determined after the preliminary exposure, the preliminary exposure condition is displayed in a colour that is less noticeable or a colour that is different from the colour displayed before the main imaging, and after the use of the preliminary exposure condition is determined, the preliminary exposure condition is displayed in a colour that is noticeable or the same colour displayed before the main imaging. Alternatively, a display shape (e.g., size, shape) may be changed. Until the preliminary exposure condition is determined after the preliminary exposure, the temporary exposure condition is displayed in a small size, and after the use of the preliminary exposure condition is determined, the preliminary exposure condition is displayed in a larger size than before. In the above example, the preliminary exposure condition is displayed from the end of the preliminary exposure; however, the preliminary exposure condition may be displayed before the preliminary exposure imaging so that the display contents of the preliminary exposure condition are varied before and after the use of the preliminary exposure condition is determined.

This enables the user to understand that the main exposure is performed with the preliminary exposure condition. Thus, when the preliminary exposure condition is not a desired condition, the user can respond such as not performing the main exposure, and as a result, the extra exposure can be reduced.

Figure 18:
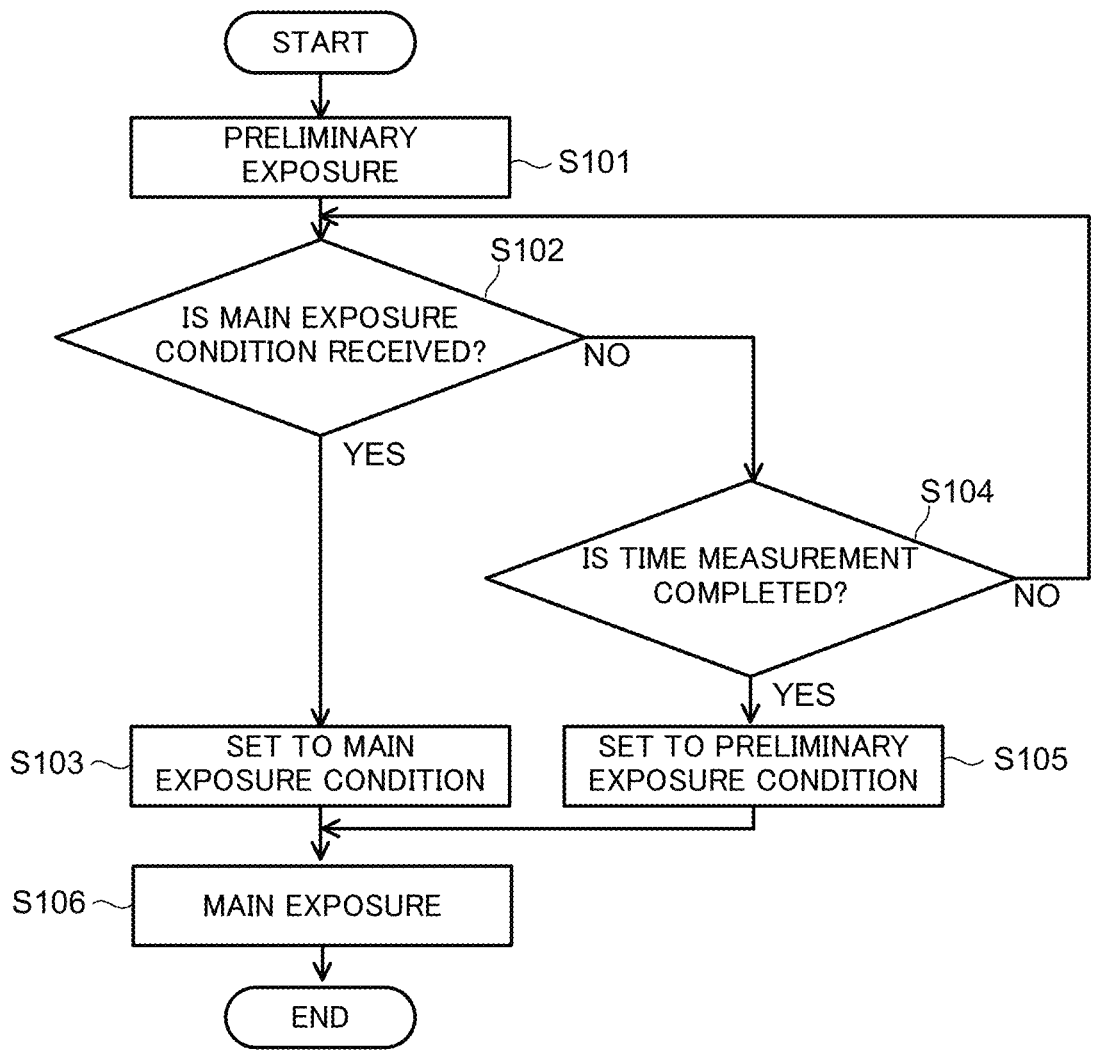
FIG. 18 is a flowchart illustrating am exemplary operation of an exposure condition setting control in a control unit.

An exemplary operation of exposure condition setting control in irradiation control unit 11B configured as above will be described. FIG. 18 is a flowchart showing an exemplary operation of the exposure condition setting control in irradiation control unit 11B. Processing in FIG. 18 is appropriately performed, for example, when imaging of an exposure image in radiation imaging system 100 is started.

As illustrated in FIG. 18, irradiation control unit 11B performs the preliminary exposure (step S101). After the end of the preliminary exposure, irradiation control unit 11B determines whether the main exposure condition has been received (step S102).

After the determination, when receiving the main exposure condition (step S102, YES), irradiation control unit 11B sets radiation irradiation apparatus 1 with the main exposure condition (step S103). On the other hand, when not receiving the main exposure condition (step S102, NO), irradiation control unit 11B determines whether time measurement is ended by measurement unit 11A (step S104).

After the determination, when the time measurement is not ended (step S104, NO), processing returns to step S102.

On the other hand, when the time measurement is ended (step S104, YES), irradiation control unit 11B sets radiation irradiation apparatus 1 with the preliminary exposure condition (step S105).

After step S103 or step S105, irradiation control unit 11B performs the main exposure (step S106).

After step S106, this control is ended.

According to the present embodiment configured as above, regardless of the derivation time of the main exposure condition based on the preliminary exposure image, the main exposure is surely started by the specific time, which enables suppressing the extension of the time between the preliminary exposure and the main exposure.

This reduces the increase in the body movement of the subject caused by the extension of the time between the preliminary exposure and the main exposure, and thus, also reduces the frequency of imaging failures in the radiation imaging system 100.

Further, since generator 11 has measurement unit 11A, a time can be measured immediately after the end of the preliminary exposure in the part when radiation is emitted. In a case where a configuration in which console 3 has a measurement unit, a time is measured after console 3 recognizes the end of the preliminary exposure by communication after the end of the preliminary exposure; therefore, the measurement start may be delayed depending on occurrence of a communication delay.

On the other hand, in the present embodiment, since the measurement is started at the timing after the end of the preliminary exposure in generator 11, the measurement time can be an accurate time.

In the above embodiment, when the preliminary exposure condition is used for the main exposure, the main exposure is performed with the preliminary exposure condition; however the present invention is not limited thereto.

Figures 19, 20:
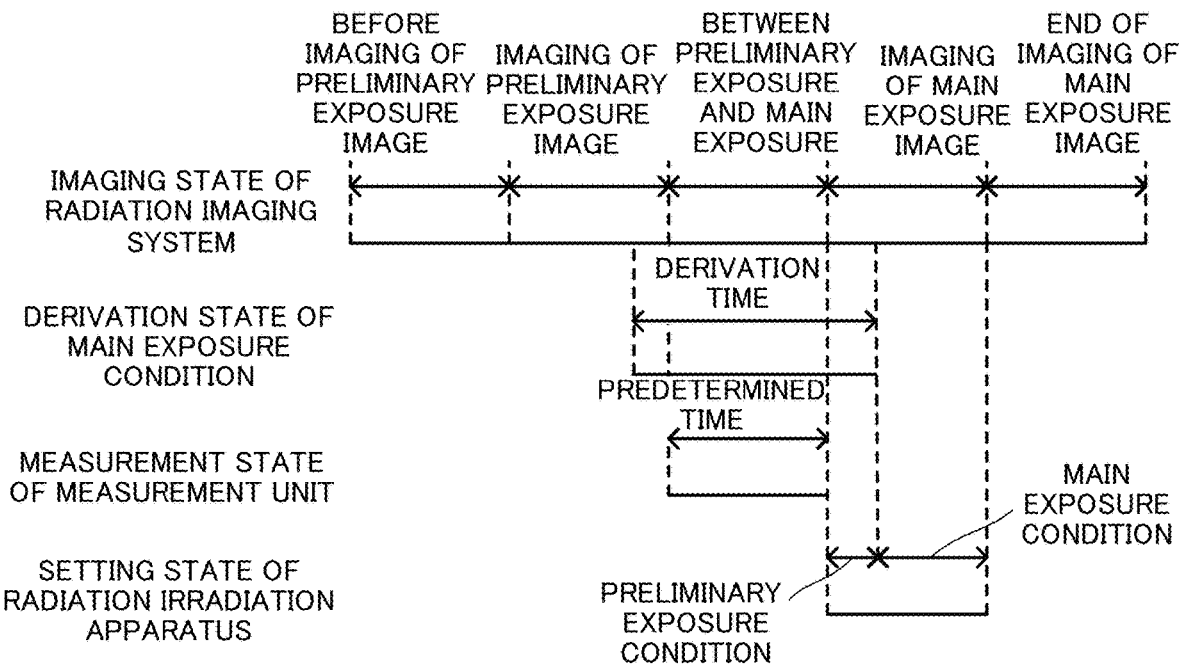
FIG. 19 illustrates an exemplary time change of each state in the radiation imaging system, the main exposure condition, the measurement unit, and the radiation irradiation apparatus.
FIG. 20 illustrates an exemplary table that contains a measurement time associated with an imaging region and an imaging direction.

For example, as illustrated in FIG. 19, the main exposure condition of the main exposure derived after the start of the main exposure with the preliminary exposure condition may be changed in the middle of the main exposure.

Specifically, when receiving the main exposure condition of the main exposure derived based on the preliminary exposure (i.e., when the derivation is ended) during the period from the start of the main exposure using the preliminary exposure condition until the end of the main exposure, irradiation control unit 11B determines whether the main exposure condition is used for the main exposure instead of the preliminary exposure condition.

Irradiation control unit 11B determines that the main exposure condition is used for the main exposure instead of the preliminary exposure condition when conditions other than the irradiation time of the radiation to the subject are the same between the main exposure condition and the preliminary exposure condition, and the irradiation time of the main exposure condition is longer than that of the preliminary exposure condition.

As a result, the main exposure with the preliminary exposure condition is substantially extended to match the irradiation time of the main exposure condition, which enables performing the exposure with an appropriate condition in the main exposure.

Irradiation control unit 11B ends the main exposure condition based on the irradiation time of the main exposure when conditions other than the irradiation time of the radiation to the subject are the same between the main exposure condition and the preliminary exposure condition, and the irradiation time of the main exposure condition is shorter than that of the preliminary exposure condition.

Thus, the main exposure is ended in the middle of the main exposure in the preliminary exposure condition. Consequently, when the irradiation time of the main exposure condition has not elapsed, the main exposure is to be performed according to the main exposure condition, and thus, the exposure can be performed with an appropriate condition in the main exposure. On the other hand, when the irradiation time of the main exposure conditions has elapsed, the main exposure is ended immediately, and thus, the extra exposure can be reduced.

In addition, in the above embodiment, when the derivation of the main exposure condition is not ended before the predetermined time elapses, it is determined that the main exposure condition cannot be used; however, the present invention is not limited thereto. For example, irradiation control unit 11B determines that the main exposure condition cannot be used when the main exposure condition of the main exposure derived based on the preliminary exposure is outside the range of the predetermined condition in radiation imaging system 100. Then, irradiation control unit 11B starts the main exposure, using the preliminary exposure condition, immediately after the determination. That is, the main exposure is started without waiting for the end of the time measurement of measurement unit 11A. This allows performing the main exposure with the small delay as much as possible The predetermined condition includes, for example, the setting condition of the relatively high value of tube voltage, tube current time product, irradiation time or the like, although the value does not cause the health risk of the subject. The predetermined condition may be compared with the main exposure condition or a condition obtained by summing the main exposure condition and the preliminary exposure condition of the preliminary exposure.

Thus, when the main exposure condition is not appropriate, the main exposure condition is not used for the main exposure, which enables suppressing the main exposure from being performed with an inappropriate main exposure condition. In the above embodiment, irradiation control unit 11B compares the main exposure condition with the predetermined condition; however, the main exposure condition derived based on the preliminary exposure by control unit 31 may be compared with the predetermined condition before transmission to generator 11, and may be transmitted to generator 11 with information indicating whether the main exposure condition is outside of range. In that case, irradiation control unit 11B determines whether the main exposure condition is outside the range of the predetermined condition using the attached information and determines that the main exposure condition cannot be used when it is outside of range. Alternatively, the main exposure condition derived based on the preliminary exposure by control unit 31 may be compared with the predetermined condition before transmission to generator 11, and when the main exposure condition is outside of the range, the transmission is made after the main exposure condition to be transmitted to generator 11 is replaced with the preliminary exposure condition.

In addition, in the above embodiment, when it is determined that the main exposure condition cannot be used, the preliminary exposure condition is used for the main exposure; however the present invention is not limited thereto. For example, irradiation control unit 11B may prohibit the main exposure.

In the manner described above, suppressing the extra exposure caused by performing the main exposure is made possible. Further, this also suppresses the useless extension of the imaging time because the main exposure is prohibited before the time between the preliminary exposure and the main exposure is extended. In the present embodiment, the main exposure is prohibited by irradiation control unit 11B; however, control unit 31 of console 3, for example, may prohibit the main exposure by transmitting the notification prohibiting the main exposure to generator 11 in a case where the main exposure condition derived based on the preliminary exposure is compared with a predetermined condition before transmission to generator 11 and is found outside of the range.

Note that, when determining that the main exposure condition cannot be used, irradiation control unit 11B may perform a first processing that prohibits the main exposure or a second processing that uses the preliminary exposure condition for the main exposure. Specifically, irradiation control unit 11B selects either one of the first processing and the second processing based on at least one or more of information on the imaging condition for the subject in radiation imaging system 100, information on the user, and information on the apparatus according to radiation imaging system 100. In this case, irradiation control unit 11B requires obtaining the information to be used for selection at the latest by the time of determining whether the main exposure condition can be used. Although details of each information will be described below, the information can be set in console 3 based on the imaging order from an external device (RIS, etc.) and the operation by the user, and thus, control unit 31 of console 3 transmits these pieces of information to irradiation control unit 11B of generator 11 at the latest by the time of determining whether the main exposure condition can be used. These pieces of information may be sent before the pre-imaging because these pieces of information are determined before the pre-imaging. This enables suppressing an increase in a communication delay due to the communication load from the pre-imaging to the start of the main imaging.

The information on the imaging condition is, for example, related to the imaging area of the subject and the imaging direction to the subject. The information on the user is, for example, related to the patient or the radiographer. The information on the apparatus is, for example, related to radiation irradiation apparatus 1 or radiation imaging apparatus 2 used in radiation imaging system 100. Further, the information on the apparatus includes information related to a configuration in which exposure switch 12 is pressed for each of the preliminary exposure and the main exposure, or a configuration in which exposure switch 12 is pressed once at the start of the preliminary exposure.

For example, irradiation control unit 11B performs the first processing that prohibits the main exposure when the imaging area of the subject is a part where the body movement of the subject (the patient) tends to increase, or when the attribute of the patient indicates tendency of a large body movement (e.g., a child). This enables reducing the frequency of imaging failures caused by the body movement of the subject.

In addition, for example, irradiation control unit 11B performs the second processing that uses the preliminary exposure condition for the main exposure when the attribute of the radiographer indicates that he or she is familiar with the system or when the patient is relatively healthy and the attribute of the user satisfies the preliminary exposure condition. This allows accurately performing both the preliminary exposure and the main exposure.

Furthermore, for example, irradiation control unit 11B may select the first processing when the apparatus is complex and select the second processing when the apparatus is simple.

In the present embodiment, irradiation control unit 11B of generator 11 selects either one of the first processing and the second processing based on at least one or more of the information on the imaging condition for the subject in radiation imaging system 100, the information on the user, and the information on the apparatus according to radiation imaging system 100; however, control unit 31 of console 3 may determine whether to select either one of the first processing and the second processing, transmit the determination contents to irradiation control unit 11B of generator 11, and irradiation control unit 11B may switch between the first processing and the second processing according to the determination contents. This eliminates the need for transmission of the information used for the selection of the first processing and the second processing such as the user information from control unit 31 of console 3 to irradiation control unit 11B of generator 11, and thus, the processing can be simplified.

Further, in a case where a configuration to perform the image addition of the preliminary exposure image based on the preliminary exposure and the main exposure image based on the main exposure is adopted and the processing such as the first processing and the second processing described above is performed, irradiation control unit 11B may instruct control unit 31 not to perform the image addition. Alternatively, control unit 31 may voluntary select whether to perform the image addition, referring to the execution information on the processing such as the first processing and the second processing described above.

For example, when the main exposure is prohibited, the image addition is unnecessary, and when the main exposure is performed using the preliminary exposure condition that is not based on the preliminary exposure image, an accurate exposure result may not be obtained even when the image addition is performed.

Note that, irradiation control unit 11B may select either one of the first processing or the second processing based on a plurality of combinations of the information on the imaging condition for the subject in radiation imaging system 100, the information on the user, and the information on the apparatus according to radiation imaging system 100 (e.g., a combination of the imaging area and an attribute of the user).

In the above embodiment, starting points of the measurement start timing by measurement unit 11A and the predetermined time are set to the end of the preliminary exposure; however, as long as they can specify the start timing of the main exposure, and the present invention is not limited thereto. For example, a timing after a certain period of time elapses from the end of the preliminary exposure may be set. However, the certain period needs to be a small value that does not exceed the limit value of the delay in starting of the main exposure that has no influence on the success or failure of imaging, which is determined beforehand by the experiments described above.

Further, an exposure start time of the preliminary exposure and a time when exposure switch 12 is pressed during the preliminary exposure may be set to the starting points of the measurement start timing and the predetermined time respectively; however, in this case, a result value of the preparation time of the preliminary exposure and a result value of the exposure time are necessary to be obtained to reflect these values in the system. For example, when a time required for the preliminary exposure varies according to the exposure time used for the preliminary exposure, a standard irradiation time of the preliminary exposure and a standard predetermined time corresponding to the standard irradiation time are determined beforehand, and then, the time obtained by adding, to the standard predetermined time, a value obtained by subtracting the standard irradiation time from the actual exposure time result value of the preliminary exposure, is set as a predetermined time. Therefore, as the starting points of the measurement start timing and the predetermined time, using the time point not affected by the variation of the time required for the preliminary exposure, such as a timing of the end of the preliminary exposure or a timing after a predetermined period elapses from the end of preliminary exposure, can simplify the processing.

Further, the maximum value of the measurement time of measurement unit 11A, that is, the predetermined time, may be determined based on at least one or more of the information on the imaging condition for the subject in radiation imaging system 100, the information on the user, and the information on the transfer time of the preliminary exposure image in the preliminary exposure.

The relation between the imaging time of radiation imaging system 100 and the magnitude of body movement of the subject differs depending on the imaging area of the subject and the imaging direction of the subject (i.e., the imaging condition for the subject). For example, a chest imaging is generally performed in a state that the patient (the subject) takes a long breath and hold the breath. However, when the imaging time is extended, the patient cannot continue to stop breathing, and thus, the body movement occurs. In this case, a short predetermined time is preferable.

On the other hand, a hand imaging from the front is generally performed in a state that the patient opens the hand on radiation imaging apparatus 2 and remains still; however, since the posture is stable, body movement of the patient hardly occurs even when the imaging time is extended.

Thus, for example, control unit 31 causes storage unit 33 to store the table illustrated in FIG. 20 and selects a predetermined time based on the imaging area and the imaging direction. In the table illustrated in FIG. 20, a predetermined time is associated with each imaging area and imaging direction.

For example, when an imaging area is the chest, and an imaging direction is set to the front, control unit 31 selects 5 seconds of No. 1 as the predetermined time. This allows appropriately adjusting the predetermined time according to the imaging conditions for the subject, and thus, the frequency of imaging failures can be reduced.

In addition, for example, when the attribute of a patient (user) indicates respiratory diseases, the patient (user) tends to be unable to stop breathing for a long time compared to a patient without respiratory diseases. Therefore, shortening the predetermined time is preferable in a case where the attribute of the patient indicates respiratory diseases.

Further, when the attribute of a patient indicates a patient with trembling hands and legs, holding the posture of the hands and legs is difficult compared to a patient without such tremors; therefore, shortening the predetermined time is preferable in a case where the patient has trembling hands and legs.

Further, when the attribute of a patient indicates an aged individual or an infant, holding the same posture is difficult; therefore, shortening the predetermined time is preferable.

Thus, for example, control unit 31 causes storage unit 33 to store the table illustrated in FIG. 21 and selects a predetermined time based on the imaging area and the imaging direction. The table illustrated in FIG. 21, a predetermined time is associated with each imaging area and imaging direction. The table also has a predetermined time based on disease correction and age correction associated with each imaging area and imaging direction. In a case where the attribute of the patient applies to a subject of the disease correction or the age correction with reference to the disease correction or the age correction, the correction described in the disease correction or the age correction is reflected in the predetermined time.

By way of example, when the imaging area is a hand and the imaging direction is set to the front, the predetermined time is 8 seconds, but when the attribute of the patient indicates tremors, −7 seconds described in the disease correction is reflected in the predetermined time. Thus, the predetermined time in this case is 1 second.

This allows adjusting the predetermined time in consideration of the disease and/or the age of the patient, and thus, the frequency of imaging failures can be reduced.

Besides, a radiographer may adjust the predetermined time by judging difficulty in holding the same posture of the patient. For example, buttons indicating the magnitude of body movement (e.g., large body movement, medium body movement, small body movement) may be installed in control unit 35 or the like, and then, the radiographer presses the appropriate button in accordance with the body movement of a patient.

For example, by setting correction values such as −4 seconds for large body movement, −2 seconds for medium body movement, and −1 second for small body movement, the predetermined time in the table illustrated in FIG. 21 can be appropriately corrected. This allows adjusting a predetermined time according to the attribute of the patient, even in a system which is not connected to the RIS and thus cannot obtain information on the patient, for example.

In addition, a transfer time of the preliminary exposure image in the preliminary exposure differs between a configuration that communicates by wire and a configuration that communicates by radio. In general, a radio communication configuration tends to require a longer transfer time than a wired communication configuration.

For example, in a configuration where the main exposure is prohibited when a main exposure condition derived based on a preliminary exposure image is abnormal due to abnormality of an apparatus, setting a predetermined time individually for the radio communication configuration and for the wired communication configuration is considered favorable. Thus, the abnormality of the main exposure condition can be accurately detected, which enables to prevent performing the main exposure by the apparatus in the abnormal state.

Further, since a method for radio communication may differ depending on a type of radiation irradiation apparatus, the predetermined time may be optimized for each type of radiation irradiation apparatus.

For example, the table illustrated in FIG. 22 and describing calculation parameters of predetermined times is stored in storage unit 33. Control unit 31, referring to the type of radiation irradiation apparatus and the communication method, obtains a transfer time of the preliminary exposure image, a standard deviation 1σ of the transfer time, and a maximum time required to prepare the main exposure condition after a transfer of the preliminary exposure image (hereinafter, the maximum time).

The transfer time of the preliminary exposure image is an average value of transfer times of the preliminary exposure image. The standard deviation 1σ of the transfer time is a value based on variation of the transfer times.

Control unit 31, for example, calculates the sum of the transfer time of the preliminary exposure image, the value obtained by multiplying the standard deviation 1σ of the transfer time by 5 (5σ), and the maximum time to set the sum as a time for determining abnormality of the apparatus (measurement time). For example, in a case where the type of the radiation irradiation apparatus is A, and the communication method is by radio, the transfer time of the preliminary exposure image is 1 second, the standard deviation 1σ is 0.2 seconds, and the maximum time is 0.5 seconds.

Control unit 31 calculates the above values, that is, 1+0.2×5+0.5=2.5 seconds as a predetermined time. Then, when the main exposure condition cannot be derived after 2.5 seconds elapse for the predetermined time, control unit 31 determines that the apparatus is under the abnormality condition.

Further, for example, the table illustrated in FIG. 23 may be prepared and stored in storage unit 33 by calculating the measurement time for each apparatus and the radio system illustrated in FIG. 22.

Thus, control unit 31 transmits the measurement time selected with reference to the table to generator 11. Generator 11 uses the predetermined time received in measurement unit 11A.

Further, the predetermined time may be adjusted by combining two or more of information on the imaging condition for a subject in the above-described radiation imaging system 100, information on the user, and information on the transfer time of the preliminary exposure image in the preliminary exposure. In this case, for example, the predetermined time to be the minimum value may be selected.

In the above embodiment, although selection of the predetermined time is performed by console 3, the selection may be performed by generator 11. In this case, a table used for the selection is stored in storage unit 11C of generator 11. In addition, an operation unit installed in generator 11 is used instead of operation unit 35, and irradiation control unit 11B is used instead of control unit 31. Furthermore, the information on the imaging condition for a subject in the above-described radiation imaging system 100, the information on the user, and the information on the transfer time of the preliminary exposure image in the preliminary exposure may be transmitted to generator 11 by console 3, and the generator may use these pieces of information.

In the above embodiment, measurement unit 11A is installed in generator 11; however, the present invention is not limited thereto. For example, measurement unit 11A may be installed in console 3 or outside radiation imaging system 100.

As in the above embodiment, when measurement unit 11A is installed in generator 11, in some cases, generator 11 needs to be customized. For example, in a case where the generator to be adopted in an expensive radiation imaging system is different from that to be used in an inexpensive radiation imaging system, the respective generators need to be customized, which incurs development periods and development costs. In contrast, a configuration in which the measurement unit is installed in console 3 is economical because no customization of respective generators is required in this configuration.

However, the configuration in which the measurement unit is installed in console 3, as described above, involves a problem in that accuracy of the measurement time is reduced.

To this problem, the accuracy of the measurement time can be increased by adding the time of the communication delay to the measurement time, through adopting a communication method having a small delay between generator 11 and console 3 or a communication method having a small variation of communication delay. For example, the problem can be solved by using a wired communication method (e.g., RS 232C or hardware signal) instead of using radio communication (e.g., IEEE 802 11 series, Bluetooth (registered trademark)) between generator 11 and console 3.

Besides, after synchronizing the time between generator 11 and console 3, generator 11 may notify console 3 of the time at a point of the end of the preliminary exposure (the time measured by the synchronized time measurement means), and console 3 may measure the elapsed time from the end of the preliminary exposure by comparing the notified time and the own synchronized time measurement means. As a method of time synchronization, for example, a time synchronization method defined by IEEE 1588 is favorably used. Using time synchronization, for example, when different cable lengths and communication speeds between console 3 and generator 11 are adopted for a plurality of radiation imaging systems individually, the communication delay difference generated by the above differences can be easily absorbed. This eliminates different settings or additional developments for the respective radiation imaging systems to be economical.

Furthermore, in the above embodiment, generator 11 has a determination unit and a processing unit. Thus, the main exposure can be started immediately after determining whether the main exposure condition or the preliminary exposure condition is used for the main exposure. Similarly, when the main exposure is performed after performing various kinds of processing based on the determination, the main exposure can be started immediately after the processing. In other words, the above embodiment prevents the time required between the end of imaging of the preliminary exposure image and the start of imaging of the main exposure image from being extremely longer than a predetermined time, thus enabling prevention of imaging failures due to body movement.

However, in the configuration in which generator 11 has the determination unit and the processing unit, in some cases, generator 11 needs to be customized. For example, in a case where the generator to be adopted in an expensive radiation imaging system is different from that to be adopted in an inexpensive radiation imaging system, the respective generators need to be customized, which incurs development periods and development costs. In contrast, adopting a configuration in which console 3 has the determination unit and the processing unit eliminates the need for customization of respective generators and thus is economical.

However, in the configuration in which console 3 has the determination unit and the processing unit, the determination result needs to be transmitted from console 3 to the generator 11 via communication after the determination, which involves an impact of a communication delay. The processing unit is also affected by the communication delay because the processing result needs to be transmitted from console 3 to generator 11. In other words, in this configuration, when the communication delay increases, the time required between the end of imaging of the preliminary exposure image and the start of imaging of the main exposure image become longer than the predetermined time by the amount of communication delay, which may increase possibility of the imaging failures due to body movement.

To solve the above problem, the predetermined time used in the measurement unit 11A is favorably set to a time obtained by subtracting the time T2, that is, the time for the communication delay from the predetermined time determined beforehand by an experiment, after adopting a communication method having a small delay between generator 11 and console 3 or a communication method having a small variation of communication delay. For example, a wired communication method (e.g., RS 232C or hardware signal) is used instead of using radio communication (e.g., IEEE 802 11 series, Bluetooth (registered trademark)) between generator 11 and console 3. Thereby, the time required between the end of imaging of the preliminary exposure image and the start of imaging of the main exposure image falls within a predetermined time determined by the experiment, which enables preventing imaging failures due to body movement.

Further, the measures as described above allows console 3 to be configured to have all of the measurement unit, the determination unit and the processing unit.

In the above embodiment, although irradiation control unit 11B or control unit 31 is configured to serve as both a determination unit and a processing unit, the present invention is not limited thereto. The determination unit and the processing unit may be configured and provided separately.

In the above embodiment, although irradiation control unit 11B of generator 11 is exemplified as the processing device, the present invention is not limited thereto. The processing device may be installed outside radiation imaging system 100.

The embodiments described above are merely examples of specific implementation of the present invention, and the technical scope of the present invention should not be restrictively interpreted by these embodiments. That is, the present invention may be implemented in various forms without departing from the spirit thereof or the major features thereof.

Although embodiments of the present invention have been described and illustrated in detail, the disclosed embodiments are made for purposes of illustration and example only and not limitation. The scope of the present invention should be interpreted by terms of the appended claims.

What is claimed is:

1. A transmission apparatus, comprising:
a transmission unit that transmits an operation state of a radiation imaging system to a user; and
a control unit that controls a state of the transmission unit, wherein
when imaging an exposure image by an exposure including a first exposure and a second exposure in the radiation imaging system, the control unit controls the state of the transmission unit such that the state of the transmission unit between the first exposure and the second exposure, the state of the transmission unit at a time of the imaging of the first exposure and the state of the transmission unit at a time of the imaging of the second exposure are a same state,
the first exposure and the second exposure are series of imaging, and
the first exposure is performed prior to the second exposure.

2. The transmission apparatus according to claim 1, wherein
two or more of the transmission units are installed, and
the control unit controls at least one of the two or more of the transmission units such that a state of the at least one of the two or more of the transmission units between the first exposure and the second exposure, the state of the at least one of the two or more of the transmission units at a time of the imaging of the first exposure and the state of the at least one of the two or more of the transmission units at a time of the imaging of the second exposure are a same state.

3. The transmission apparatus according to claim 2, wherein
the control unit sets a second transmission unit other than a first transmission unit to be in a state different from that of the first transmission unit between the first exposure and the second exposure, the first transmission unit having been set to be in the state based on that at the time of the imaging of the exposure image.

4. The transmission apparatus according to claim 2, wherein
the control unit is capable of selecting a plurality of transmission patterns including a combination of states between the first exposure and the second exposure in the two or more of the transmission units and sets one transmission pattern selected from among the plurality of transmission patterns to be a state of the two or more of the transmission units.

5. The transmission apparatus according to claim 4, wherein
the control unit selects the one transmission pattern based on at least one of information on the user and information on an apparatus related to the radiation imaging system.

6. The transmission apparatus according to claim 1, wherein
the transmission unit comprises a device that acts on at least one of a visual sense, a hearing sense or a tactile sense of the user.

7. The transmission apparatus according to claim 1, wherein
the control unit decides an imaging condition for performing the second exposure, based on a preliminary exposure image obtained by the first exposure performed prior to the second exposure and on information related to the preliminary exposure image.

8. The transmission apparatus according to claim 7, wherein
the imaging condition is an imaging condition for combining the preliminary exposure image obtained by the first exposure and a main exposure image obtained by the second exposure.

9. A radiation imaging system, comprising:
a radiation irradiation apparatus that emits radiation for exposure;
a radiation imaging apparatus that generates image data of an exposure image by receiving an exposure of the radiation; and
the transmission apparatus according to claim 1.

10. The radiation imaging system according to claim 9, wherein
the transmission unit and the control unit are installed in the radiation irradiation apparatus.

11. The radiation imaging system according to claim 10, wherein
an imaging condition for performing the second exposure, which are determined based on information on a preliminary exposure image, is an imaging condition related to a dose or an irradiation time.

12. The radiation imaging system according to claim 9, wherein the transmission unit is installed in the radiation irradiation apparatus, and the control unit is installed in the radiation imaging apparatus.

13. The radiation imaging system according to claim 9, wherein the transmission unit is a lamp that is included in a hand switch used by the user to operate the radiation imaging system.

14. The transmission apparatus according to claim 1, wherein the first exposure is performed at a dose lower than a dose of the second exposure.

15. The transmission apparatus according to claim 1, wherein the exposure image is imaged without operating an exposure switch between the first exposure and the second exposure.

16. The transmission apparatus according to claim 1, wherein a plurality of the second exposure are performed after the first exposure.

17. A transmission control apparatus that controls a transmission unit that transmits an operation state of a radiation imaging system to a user, the transmission control apparatus comprising a control unit that decides a state of the transmission unit and controls the transmission unit such that the transmission unit is in the decided state of the transmission unit, wherein when imaging an exposure image by an exposure including a first exposure and a second exposure in the radiation imaging system, the control unit controls the state of the transmission unit such that the state of the transmission unit between the first exposure and the second exposure, the state of the transmission unit at a time of the imaging of the first exposure and the state of the transmission unit at a time of the imaging of the second exposure are a same state, the first exposure and the second exposure are series of imaging, and the first exposure is performed prior to the second exposure.

* * * * *